United States Patent
Mitchell et al.

(10) Patent No.: US 11,145,395 B1
(45) Date of Patent: Oct. 12, 2021

(54) HEALTH HISTORY ACCESS

(71) Applicants: Laura A. Mitchell, Millville, NJ (US); Robert W. Dickson, III, Greenwich, NJ (US)

(72) Inventors: Laura A. Mitchell, Millville, NJ (US); Robert W. Dickson, III, Greenwich, NJ (US)

(*) Notice: Subject to any disclaimer, the term of this patent is extended or adjusted under 35 U.S.C. 154(b) by 48 days.

(21) Appl. No.: 16/928,020

(22) Filed: Jul. 14, 2020

Related U.S. Application Data

(60) Provisional application No. 62/874,714, filed on Jul. 16, 2019.

(51) Int. Cl.
  *G16H 10/60* (2018.01)
  *G16H 50/20* (2018.01)
  *G16H 30/40* (2018.01)

(52) U.S. Cl.
  CPC ............ *G16H 10/60* (2018.01); *G16H 30/40* (2018.01); *G16H 50/20* (2018.01)

(58) Field of Classification Search
  CPC ........ G16H 10/60; G16H 30/40; G16H 50/20; G06T 19/00; G06T 2200/24; G06T 2219/004; G06F 17/278
  See application file for complete search history.

(56) References Cited

U.S. PATENT DOCUMENTS

| | | |
|---|---|---|
| 8,645,164 B2 | 2/2014 | Faiola et al. |
| 9,199,122 B2 | 12/2015 | Kaleal, III et al. |
| 10,037,820 B2 | 7/2018 | Wong et al. |
| 10,366,624 B2 | 7/2019 | Dawson et al. |
| 2011/0270751 A1* | 11/2011 | Csinger .................. H04L 63/18 705/42 |

(Continued)

FOREIGN PATENT DOCUMENTS

WO    WO-2019159007 A1 *   8/2019    ............. G16H 50/20

OTHER PUBLICATIONS

Hsu, Using Knowledge Encoded in Graphical Disease Models to Support Context-Sensitive Visualization of Medical Data, 2009, UMI ProQuest, pp. 1-217. (Year: 2009).*

*Primary Examiner* — Christopher L Gilligan
(74) *Attorney, Agent, or Firm* — 21st Century IP LLC; Kelly Hollowell

(57) ABSTRACT

Apparatus and associated methods relate to receiving a patient health record, determining a relationship between the health record and the patient health history, determining a condition associated with the health record and the location on the patient's body affected by the condition, and automatically presenting the relationship between the health record and health history based on the condition. In an illustrative example, the patient health record may be a doctor's diagnosis. The relationship between the health record and the patient health history may link multiple health records medically related to the received health record. In some examples, the relationship between the health record and health history may be comorbidity. The health history may include conditions complicating the condition associated with the health record. Various examples may advantageously present the patient's health status and conditions interactively visualized as a function of the patient's body, and the medical condition type or severity.

20 Claims, 21 Drawing Sheets

(56) References Cited

U.S. PATENT DOCUMENTS

| | | | | |
|---|---|---|---|---|
| 2014/0172864 A1* | 6/2014 | Shum | ............... | G06F 19/00 |
| | | | | 707/740 |
| 2016/0019352 A1* | 1/2016 | Cohen | ............... | G16H 10/60 |
| | | | | 705/3 |
| 2016/0378922 A1* | 12/2016 | Shiu | ............... | G16H 10/60 |
| | | | | 705/2 |
| 2018/0091511 A1* | 3/2018 | Vendrell | ............... | H04L 63/10 |
| 2018/0181716 A1* | 6/2018 | Mander | ............... | G06Q 10/0633 |
| 2019/0189253 A1* | 6/2019 | Kartoun | ............... | G16H 50/30 |
| 2019/0259481 A1* | 8/2019 | Chan | ............... | G16H 15/00 |
| 2020/0027532 A1* | 1/2020 | White | ............... | G06F 40/295 |
| 2020/0160946 A1* | 5/2020 | Poblenz | ............... | G06K 9/3233 |
| 2020/0381127 A1* | 12/2020 | Silverman | ............... | G16H 50/20 |

* cited by examiner

400 →

```
┌─────────────────────────────────────────────────────────────────────┐
│ Determine the type, severity, body location, affected organs, and prior procedure or │
│ onset date of the medical condition associated with a received health record   405  │
└─────────────────────────────────────────────────────────────────────┘
                                    │
                                    ▼
                              ╱ 410 ╲       Yes      ┌──────────────────┐
                             ╱Is Condition╲─────────▶│ Flag condition as │
                             ╲ Systemic   ╱          │   systemic   415  │
                              ╲    ?    ╱            └──────────────────┘
                                  │ No                        │
                                  ▼◀───────────────────────────┘
                              ╱ 420 ╲       Yes      ┌──────────────────┐
                             ╱Is Condition╲─────────▶│ Flag condition as │
                             ╲  Severe    ╱          │    severe   425   │
                              ╲    ?    ╱            └──────────────────┘
                                  │ No                        │
                                  ▼◀───────────────────────────┘
┌─────────────────────────────────────────────────────────────────────┐
│ Compare medical condition type, severity, organs affected, complicating              │
│ factors, body location, prior procedures, and onset date with patient health         │
│ history, to determine if the medical condition is related to one or more health      │
│ record comprising the health history, based on the comparison      430              │
└─────────────────────────────────────────────────────────────────────┘
                                    │
                                    ▼
                    No        ╱ 435 ╲
          ◀────────────────── Is Condition
                              Related to
                              History
                                ?
                                    │ Yes
                                    ▼
                              ╱ 440 ╲       Yes      ┌──────────────────┐
                             ╱Is Condition╲─────────▶│  Update health   │
                             ╱Related by  ╲          │ history to link   │
                             ╲  organs    ╱          │ new record with   │
                              ╲ affected ╱           │ history based    │
                                ╲  ?   ╱             │  on organs       │
                                  │ No               │ affected  445    │
                                  ▼                  └──────────────────┘
                                                              │
          │                       ▼◀───────────────────────────┘
          ▼                       ▼
    To step 480,            To step 450,
      FIG. 4B                 FIG. 4B
```

Type: Condition

Description: High Blood Pressure

Date: 2015

Category: Systemic

Status: Moderate, Ongoing

610

Type: Procedure

Description: Tonsillectomy

Date: 1992

Category: Non-systemic

Status: Not Severe

615

Type: Procedure

Diagnosis: Aortic Arch Replacement

Date: 2017

Category: Systemic

Status: Critical

620

Type: Medication

Description: Blood Pressure Medication

Date: 2015

Category: Systemic

Status: Critical, Ongoing

625

Type: Condition

Diagnosis: Deep Vein Thrombosis

Date: 2019

Category: Systemic

Status: Critical, Recovered

630

Type: Injury

Diagnosis: Broken Wrist

Date: 1998

Category: Non-systemic

Status: Not Severe, Recovered

FIG. 6A

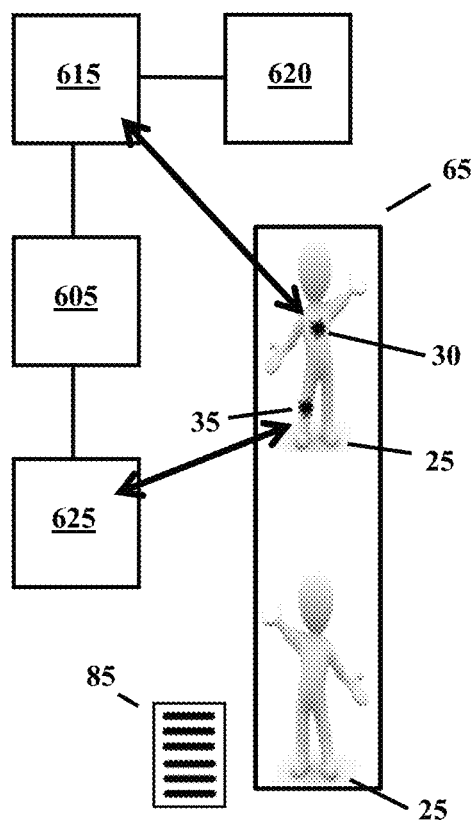
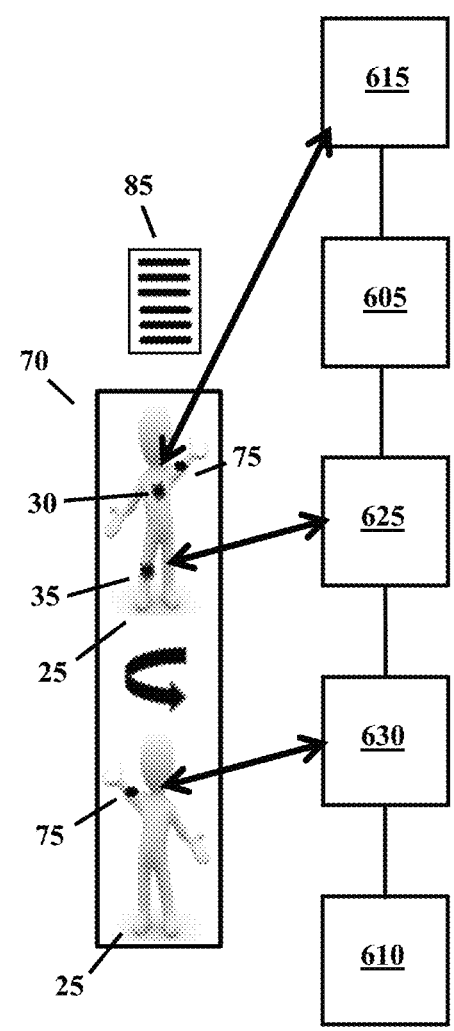
FIG. 6B
FIG. 6C

New Hospitalizations

Any hospital visits you have had.

748  Home / My Health / Hospitalizations / New Record

Details | Files

- 750a — Diagnosis*: heart
- 750b — Event Date: Month / Day / Year
- 750c — Related Life Event: None
- 750d — Diagnosing Professional: ☐ Robert Dickson
- 750e — Insurance Provider: ☐ Medicare
- 750f — Details*
- 750g — Prescriptions

- 744e — Where  — 750h
- 744f — Front or Back
- 744g — Left or Right
- 744h — Pertinence*

Dropdown options (750h):
- Everywhere
- Head
- Shoulder
- Thorax
- Abdomen
- Pelvis
- Upper Arm
- Elbow
- Lower Arm
- Hand or Wrist
- Upper Leg (Thigh region)
- Knee
- Lower Leg (Shin region)
- Foot or Ankle
- Neck

FIG. 7J

HEALTH HISTORY ACCESS

CROSS-REFERENCE TO RELATED APPLICATIONS

This application claims the benefit of U.S. Provisional Application No. 62/874,714, titled "System for Managing and Displaying Health Related Data of a Patient," filed by Laura A. Mitchell and Robert W. Dickson III, on Jul. 16, 2019. This application incorporates the entire contents of the above-referenced application herein by reference.

TECHNICAL FIELD

Various embodiments relate generally to health history.

BACKGROUND

Health is a state of being. A person's health may be good, poor, improving, or declining, depending on the state of the person's physical, mental, or emotional condition. Health may be improved or maintained by treating or screening for medical conditions. For example, a health care provider may screen or treat a patient for a medical condition using various methods, including diagnostic laboratory tests, examination, surgery, medication, or analysis of the patient's health history.

Users of health history include patients, health care providers, and insurers. Users may access a patient's health history to help evaluate a medical condition, for diagnosis or treatment. A person may experience many medical conditions over time. For example, each medical condition new to a patient may be diagnosed or treated by a health care provider. Some medical diagnosis, treatment, or examination outcomes may be recorded by a health care provider. A patient's health history may include many such health records. Effective diagnosis or treatment for a medical condition may depend on data related to more than one health record included in the patient's health history. During a patient's lifetime, the patient may receive many diagnoses and treatments from multiple health care providers in different locations.

A patient's health records may include a variety of information useful to a health care provider treating the patient. For example, a patient's health records may record a medical procedure, diagnosis, condition, diagnostic test, or prescription. Some conditions may be serious. In an illustrative example, a serious condition may be complicated by another condition new to a patient. A health care provider treating a patient for the first time may need to request the patient's complete health history. In some cases, a patient may forget to tell the health care provider about a past procedure or condition. A patient with many health records may expend substantial effort relaying their health history to a health provider.

SUMMARY

Apparatus and associated methods relate to receiving a patient health record, determining a relationship between the health record and the patient health history, determining a condition associated with the health record and the location on the patient's body affected by the condition, and automatically presenting the relationship between the health record and health history based on the condition. In an illustrative example, the patient health record may be a doctor's diagnosis. The relationship between the health record and the patient health history may link multiple health records medically related to the received health record. In some examples, the relationship between the health record and health history may be comorbidity. The health history may include conditions complicating the condition associated with the health record. Various examples may advantageously present the patient's health status and conditions interactively visualized as a function of the patient's body, and the medical condition type or severity.

In an aspect, a process is provided, comprising: receiving a patient health record; determining a relationship between the health record and patient health history, wherein the health history comprises a plurality of linked health records; determining a condition associated with the health record; determining a location on the patient's body affected by the condition; and, automatically presenting the relationship between the health record and health history based on the condition.

Presenting the relationship between the health record and health history based on the condition may further comprise the patient's health history interactively visualized on a model of the patient's body.

The patient's health history interactively visualized on the model of the patient's body may further comprise the model of the patient's body visibly marked to indicate the location on the patient's body affected by the condition associated with the health record.

The model of the patient's body visibly marked to indicate the location on the patient's body affected by the condition associated with the health record may further comprise the marked location on the visualized model clickable to display when clicked a health record medically related to the patient condition.

Determining the condition associated with the health record may further comprise categorizing the condition as systemic or non-systemic, and presenting the relationship between the health record and health history may further comprise presenting a systemic condition marked visually distinct from a non-systemic condition on a model of the patient's body.

Presenting the relationship between the health record and health history may further comprise visibly marking the model of the patient's body to present a systemic condition earlier in time than a non-systemic condition.

Determining the condition associated with the health record may further comprise determining a condition degree of severity, and presenting the relationship between the health record and health history may further comprise visibly marking a model of the patient's body to present a more severe condition earlier in time than a less severe condition, based on the degree of severity.

Determining the condition associated with the health record may further comprise determining a condition degree of severity, and presenting the relationship between the health record and health history may further comprise visibly marking a model of the patient's body to present a more severe condition as visually distinct from a less severe condition, based on the degree of severity.

Presenting the relationship between the health record and health history based on the condition may further comprise evaluating the condition to determine if the condition medically complicates another condition in the health history.

In another aspect, an apparatus is provided, comprising: a processor; a user interface, operably coupled with the processor; and, a memory, operably coupled with the processor, wherein the memory encodes processor executable program instructions and data to program and configure the processor to cause the apparatus to perform operations comprising: receive a patient health record comprising a plurality of data fields encoding patient health information; determine a relationship between the received health record and patient health history, wherein the health history comprises a plurality of linked health records, and wherein each health record of the plurality of linked health records comprising the health history comprises a plurality of data fields encoding patient health information, and wherein the relationship between the received health record and the patient health history is determined as a function of comparing the received health record with at least a portion of the plurality of linked health records comprising the health history; determine a medical condition associated with the received health record and a location on the patient's body affected by the condition; categorize the medical condition as systemic or non-systemic based on medical diagnosis data encoded by the received health record, wherein the categorization is determined as a function of comparing the diagnosis data encoded by the received health record with predetermined data representative of possible diagnoses; update the health history by linking the received health record with the health history, based on associating patient health information encoded by the received health record with patient health information encoded by at least one health record comprising the health history; and, automatically present in the user interface the relationship between the received health record and health history interactively visualized on a model of the patient's body, wherein the relationship is based on the condition and the location on the patient's body affected by the condition, visibly marking the model of the patient's body to indicate the location on the patient's body affected by the condition associated with the health record.

The plurality of linked health records comprising the health history may be linked to form a collection of health records associated based on comparing data encoded by the patient health information data fields between the health records.

The data compared between the health records may further comprise diagnosis data.

The data compared between the health records may further comprise procedure data.

The data compared between the health records may further comprise life event data.

The operations performed by the apparatus may further comprise: in response to detecting in the user interface a selection of an affected patient body location marked on the model of the patient's body, displaying in the user interface a user selectable list of the linked health records comprising the health history associated with the selected location.

The operations performed by the apparatus may further comprise: in response to detecting in the user interface a user engagement with a user interface control governing orientation of the model of the patient's body, display the model of the patient's body reoriented as a function of the user engagement with the orientation control.

In another aspect, an apparatus is provided, comprising: a processor; a user interface, operably coupled with the processor; and, a memory, operably coupled with the processor, wherein the memory encodes processor executable program instructions and data to program and configure the processor to cause the apparatus to perform operations comprising: receive a patient health record comprising a plurality of data fields encoding patient health information; determine a relationship between the received health record and health history, wherein the health history comprises a plurality of linked health records, wherein each health record of the plurality of linked health records comprising the health history comprises a plurality of data fields encoding patient health information, wherein the relationship between the received health record and the patient health history is determined as a function of comparing the received health record with at least a portion of the plurality of linked health records comprising the health history, wherein the plurality of linked health records comprising the health history are linked to form a collection of health records associated based on comparing data encoded by the patient health information data fields between the health records, and wherein the data compared between the health records further comprises at least one of: diagnosis, procedure, life event, condition, complicating condition, or onset date data; determine a medical condition associated with the received health record and a location on the patient's body affected by the condition; categorize the medical condition as systemic or non-systemic based on medical diagnosis data encoded by the received health record, wherein the categorization is determined as a function of comparing the diagnosis data encoded by the received health record with predetermined data representative of possible diagnoses; update the health history by linking the received health record with the health history, based on associating patient health information encoded by the received health record with patient health information encoded by at least one health record comprising the health history; automatically present in the user interface the relationship between the received health record and health history interactively visualized on a model of the patient's body, wherein the relationship is based on the condition and a location on the patient's body affected by the condition, visibly marking the model of the patient's body to indicate the location on the patient's body affected by the condition associated with the health record; in response to detecting in the user interface a selection of an affected patient body location marked on the model of the patient's body: displaying in the user interface a user selectable list of the linked health records comprising the health history associated with the selected location; and, in response to detecting in the user interface a user engagement with a user interface control governing orientation of the model of the patient's body, display the model of the patient's body reoriented as a function of the user engagement with the orientation control.

At least a portion of the operations performed by the apparatus may be implemented by a SaaS (Software as a Service) application executing as a cloud service.

The operations performed by the apparatus may further comprise denying health history access to a user until successful authentication by the user.

Authentication may be determined as a function of a QR code visually transmitted as a function of telemedicine.

Various embodiments may achieve one or more advantages. For example, some embodiments may improve a user's ease of access to health history. This facilitation may be a result of reducing the user's effort searching health records, and adjusting relationships between the user's health records to configure health information in the user's health history. In some embodiments, health records may be automatically linked to generate an interactive health history presentable to a user's doctor. Such automatic health history generation may reduce a user's exposure to omitting details when relaying health history to a doctor. Some embodiments may interactively present medical information related to a user's health history with reference to the location on the patient's body affected by a medical condition. Such an interactive health history presentation indexed by patient body location may reduce a user's effort relaying important medical records to a doctor. In some examples, a doctor may selectively access health history based on patient body location, permitting the doctor to navigate to the health records most important to the doctor's examination considering each body location.

Various implementations may improve a doctor's effectiveness obtaining crucial health information from a patient new to the doctor. This facilitation may be a result of interactively visualizing a patient's health history on a three-dimensional model of the patient's body. In an illustrative example, the three-dimensional model of the patient's body may be visibly marked to indicate the body location affected by each patient medical condition, permitting a doctor's click on the modeled location to reorient the model and provide the doctor access to health records related to the location. For example, the user selectable health history visualized on the reorientable model of the patient's body may permit a doctor to survey a patient's health history more quickly, improving the accuracy or usefulness of obtaining patient information.

In some embodiments, the effort required by a doctor to identify related medical conditions based on the patient's health history may be reduced. Such reduced effort identifying related medical conditions may be a result of presenting medically related conditions linked to permit user navigation from each condition to a related or complicating condition. For example, a doctor accessing a patient heart condition record after clicking the corresponding location on a model of the patient's body may be provided a selectable link to a condition complicating or related to the heart condition. Some embodiments may improve the efficiency of relaying important medical history information to a doctor. This facilitation may be a result of visibly marking severe or systemic conditions visibly distinct from non-systemic or less severe conditions, at the affected patient body locations on the model of the patient's body. For example, a doctor may navigate to systemic or severe conditions first, following links to related or complicating conditions, to quickly gain a more thorough understanding of the patient's serious conditions before proceeding to less serious conditions. Some designs may increase the availability of a patient's health history to multiple health care providers. This facilitation may be a result of providing a patient's health history through a cloud service, permitting multiple health care providers to interactively access the patient's health history.

The details of various embodiments are set forth in the accompanying drawings and the description below. Other features and advantages will be apparent from the description and drawings, and from the claims.

BRIEF DESCRIPTION OF THE DRAWINGS

FIGS. 4A-4B together depict a process flow of an exemplary Health History Access Engine (HHAE) providing access to a user's health history in an exemplary health history comprehension mode driven by health record ingest.

FIGS. 6A-6C together depict illustrative examples of health history based on associated health record data.

FIGS. 7A-7J together depict various views of exemplary health record input scenarios.

Like reference symbols in the various drawings indicate like elements.

DETAILED DESCRIPTION OF ILLUSTRATIVE EMBODIMENTS

To aid understanding, this document is organized as follows. First, visual access to health history formed from adaptively linked patient health records interactively presented on a visual patient anatomical model is briefly introduced with reference to FIG. 1A. Second, with reference to FIGS. 2-3, the discussion turns to examples that illustrate health history access system component design. Specifically, health history access network and computing device implementations are disclosed. Third, with reference to FIGS. 4A-5B, exemplary process flows of an illustrative Health History Access Engine (HHAE) in exemplary health history comprehension and visual navigation modes are described. Then, with reference to FIGS. 6A-6C, an illustrative example of adaptively linking health records to construct visualized interactive health history is disclosed. Finally, with reference to FIGS. 7A-7J and FIGS. 8A-8D, exemplary health record input and health history model visualization scenarios are presented to explain improvements in health history access technology.

Figure 1A:
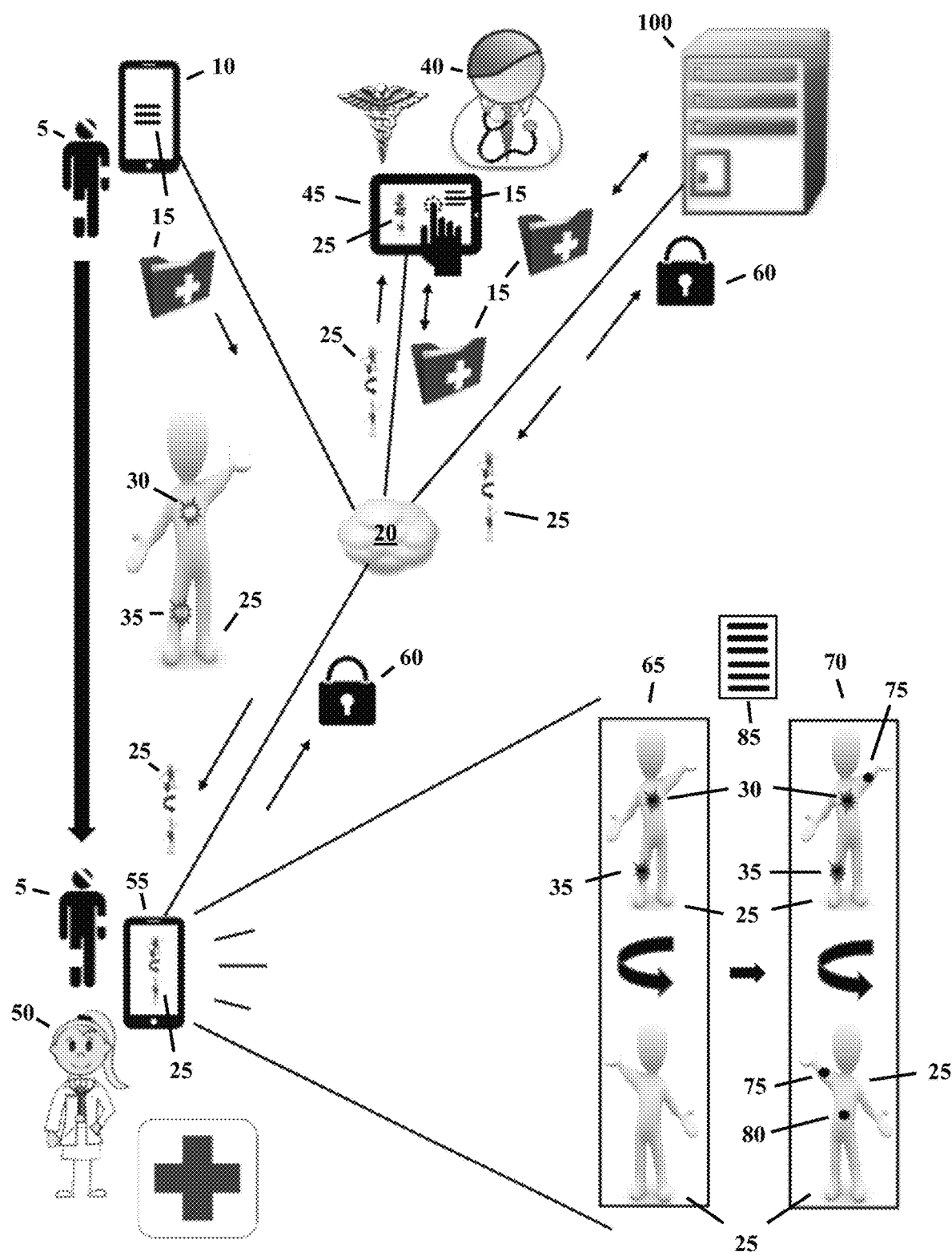
FIGS. 1A-1B together depict an illustrative operational scenario wherein a user employs an exemplary health history access service configured to provide access to the user's health history based on receiving a patient health record, determining a relationship between the health record and the patient health history, determining a condition associated with the health record and the location on the patient's body affected by the condition, and automatically presenting the relationship between the health record and health history based on the condition.
Figure 1B:
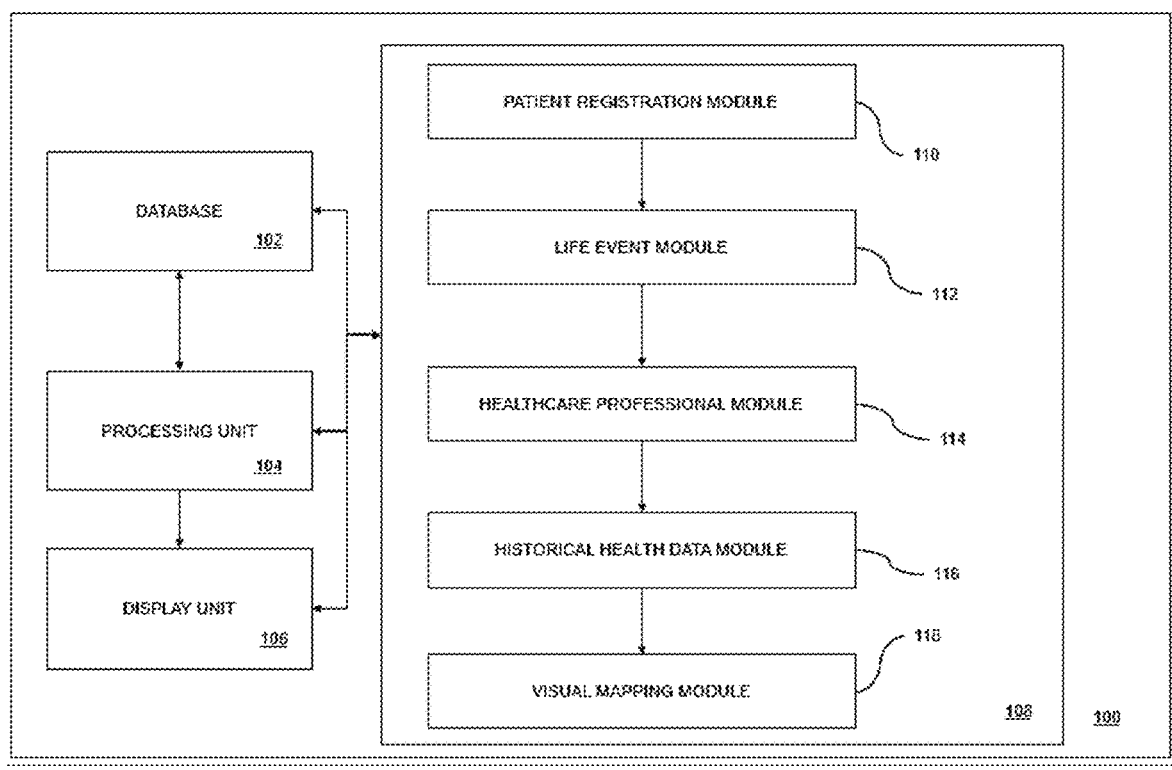

FIGS. 1A-1B together depict an illustrative operational scenario wherein a user employs an exemplary health history access service configured to provide access to the user's health history based on receiving a patient health record, determining a relationship between the health record and the patient health history, determining a condition associated with the health record and the location on the patient's body affected by the condition, and automatically presenting the relationship between the health record and health history based on the condition.

In FIG. 1A, the user 5 employs the mobile device 10 to enter health records 15 into the health history access system 100 via the network cloud 20. In the depicted example, the user 5 is a medical patient. The health records 15 may include medical records of the medical patient 5, such as, for example, diagnoses, surgeries, procedures, medications, life events, and health provider details. In the illustrated example, the health history access system 100 receives the medical patient 5 health records 15. In this example, the health history access system 100 determines a relationship between each of the health records 15 and the medical patient 5 health history constructed based on identifying relationships between individual health records and linking related health records. In this example, the health history access system 100 determines a condition associated with each of the health records 15 and the location on the medical patient 5 body affected by the condition, and automatically constructs the health history model 25 displayed on an interactive medical patient 5 body visualization, to present the relationship between the health records 15 and the medical patient 5 health history based on the condition. In the depicted example, the health history model 25 display includes selectable visual indications marking medical patient 5 body locations affected by medical conditions. In the illustrated example, the medical patient 5 body locations marked include the chest 30 indicating an aortic arch replacement record and the leg 35 indicating a deep vein thrombosis record. In the depicted example, the medical doctor 40 accesses the medical patient 5 health history model 25 through the mobile device 45 and the health history access system 100. In the illustrated example, the chest 30 is selectable in the health history model 25 displayed in the medical doctor 40 mobile device 45, to permit the medical doctor 45 access to the health records related to the medical patient 5 aortic arch replacement. In the depicted example, the leg 35 is selectable in the health history model 25 displayed in the medical doctor 40 mobile device 45, to permit the medical doctor 45 access to the health records related to the medical patient 5 deep vein thrombosis. The medical doctor 45 interactively and selectively accesses the medical patient 5 health history model 25 presented in the mobile device 45, to review the medical patient 5 health records 15 associated with the patient body locations marked on the health history model 25. In the illustrated example, the medical patient 5 visits the medical doctor 50 for urgent medical attention. The visit may be a telemedicine visit. The medical patient 5 is new to the medical doctor 50. The medical doctor 50 does not have access to the medical patient 5 health history. In this example, the medical patient 5 must relay the relevant medical patient 5 health history to the medical doctor 50, to facilitate effective treatment by the medical doctor 50. In the depicted example, the medical doctor 50 uses the mobile device 55 for authentication 60 with the health history access system 100, to access the medical patient 5 health history model 25. Authentication 60 may be, for example, a function of a cryptographically secure credential provided by the medical doctor 50. In the illustrated example, the medical doctor 50 initially selects the systemic aspect 65 of the health history model 25, to review the more severe, systemic, and potentially complicating medical conditions more quickly. In the depicted example, the systemic aspect 65 of the health history model 25 interactively presented to the medical doctor 50 in the mobile device 55 includes the chest 30 indicating the aortic arch replacement record and the leg 35 indicating the deep vein thrombosis record. The medical doctor 50 interactively and selectively accesses the medical patient 5 health history model 25 presented in the mobile device 55, reviewing the medical patient 5 health history associated with the marked patient body locations affected by systemic or severe conditions presented in the systemic aspect 65 of the health history model 25, including the chest 30 and the leg 35. After reviewing the more serious medical conditions and affected body locations presented in the systemic aspect 65 of the health history model 25, the medical doctor selects the standard aspect 70 of the health history model 25, to review less serious conditions including non-systemic conditions. In the illustrated example, the standard aspect 70 of the health history model 25 interactively presented to the medical doctor 50 in the mobile device 55 includes the wrist 75 indicating a broken wrist record and the lower back 80 indicating a back pain record. The medical doctor 50 may navigate the health history model by clicking on a patient body location visibly marked on the health history model 25 in the mobile device 55 user interface. In the depicted example, the systemic or severe conditions 30 and 35 are marked visually distinct from the non-systemic or less serious conditions 75 and 80. When the medical doctor 50 clicks on a patient body location, the health records related to the location clicked may be presented in the user selectable health record list 85. The medical doctor 50 may navigate the health history by clicking a health record in the user selectable health record list 85. When the medical doctor 50 clicks on a health record in the user selectable health record list 85, the clicked health record, and health records related to the clicked health record, may be presented in the mobile device 55. When the medical doctor 50 clicks on a health record in the user selectable health record list 85, the medical patient 5 health history model 25 visual presentation in the mobile device 55 may be reoriented to automatically provide the medical doctor 50 with visual access to the areas of the medical patient 5 body affected by medical conditions encoded in the medical patient 5 health history model 25. As the medical doctor 50 navigates the medical patient 5 health history model 25 presented in the mobile device 55, the medical doctor may engage a user interface control implemented in the mobile device 55 to govern the health history model 25 visualization pan, tilt, and zoom parameters, reorienting the visualization in three dimensions. In an illustrative example, in a telemedicine session, the medical patient 5 may facilitate authentication 60 of the medical doctor 50 based on visually presenting a QR code to a camera in the medical patient 5 mobile device 10 for transmission to the medical doctor 50 mobile device 55 display. The QR code displayed on the mobile device 55 may be scanned by the medical doctor 50 and presented to the health history access system 100 to facilitate the authentication 60. The QR code visually presented by the medical patient 5 may be, for example, fixed, and retained in a bracelet or other accessory. The QR code visually presented by the medical patient 5 may be, for example, generated on-demand by the medical patient 5 mobile device 10, based on a cryptographically secure pseudorandom number generator. The QR code may be, for example, presented to the health history access system 100 with a one-time password generated by the medical patient 5 mobile device 10. The one-time password may be valid for a limited period of time determined as a function of collaboration between the medical patient 5 mobile device 10 and the health history access system 100. The health history access system 100 may require the medical doctor 50 to provide QR code data in combination with a password, before allowing access to the medical patient 5 health history model 25 in the medical doctor 50 mobile device 55.

In FIG. 1B, the block diagram of the exemplary health history access system 100 includes the database 102, the processing unit 104 and the display unit 106. The display unit 106 may include a graphical user interface. The database 102 is configured to store the plurality of modules 108. The processing unit 104 is coupled to the database 102 to process the plurality of modules 108. The processing unit 104 may be referred to as the processor 104 or the CPU (Central Processing Unit) 104. In the depicted example, the display unit 106 is coupled to the processor 104 to display the processed plurality of modules 108. In the illustrated example, the plurality of modules 108 includes the patient registration module 110, the life event module 112, the healthcare professional module 114, the historical health data module 116, and the visual mapping module 118. In the depicted example, the patient registration module 110 is configured to register a patient's personal information on the database 102. In the illustrated example, the life event module 112 is configured to receive the patient's life event details related to health issues. In the illustrated example, the healthcare professional module 114 is configured to receive the patient's healthcare professional information. In the depicted example, the historical health data module 116 is configured to receive the patient's historical health data. In the illustrated example, the visual mapping module 118 is configured to provide a three-dimensional visual output of the patient's anatomy mapped with the patient's health data and life event details.

The plurality of modules 108 may include an insurance module configured to receive current or past insurance providers, including their insurance identification or policy number, the provider of the insurance, for example an employer, spouse's employer, Medicare, Medicaid, and the like. In an illustrative example, the user may enter the name address, phone, fax, website, and email of the insurance provider. The user may attach copies of their insurance cards or other documentation related to their insurance files.

The plurality of modules 108 may include a pharmacy module configured to receive current or past pharmacies, including the name, address, phone, fax, email, and website. The user may also attach prescriptions or files to the information on each pharmacy they add to their history. The user is able to view the pharmacies associated with each medication and thus is able to quickly order without wasting time in finding the right pharmacies.

Figure 2:
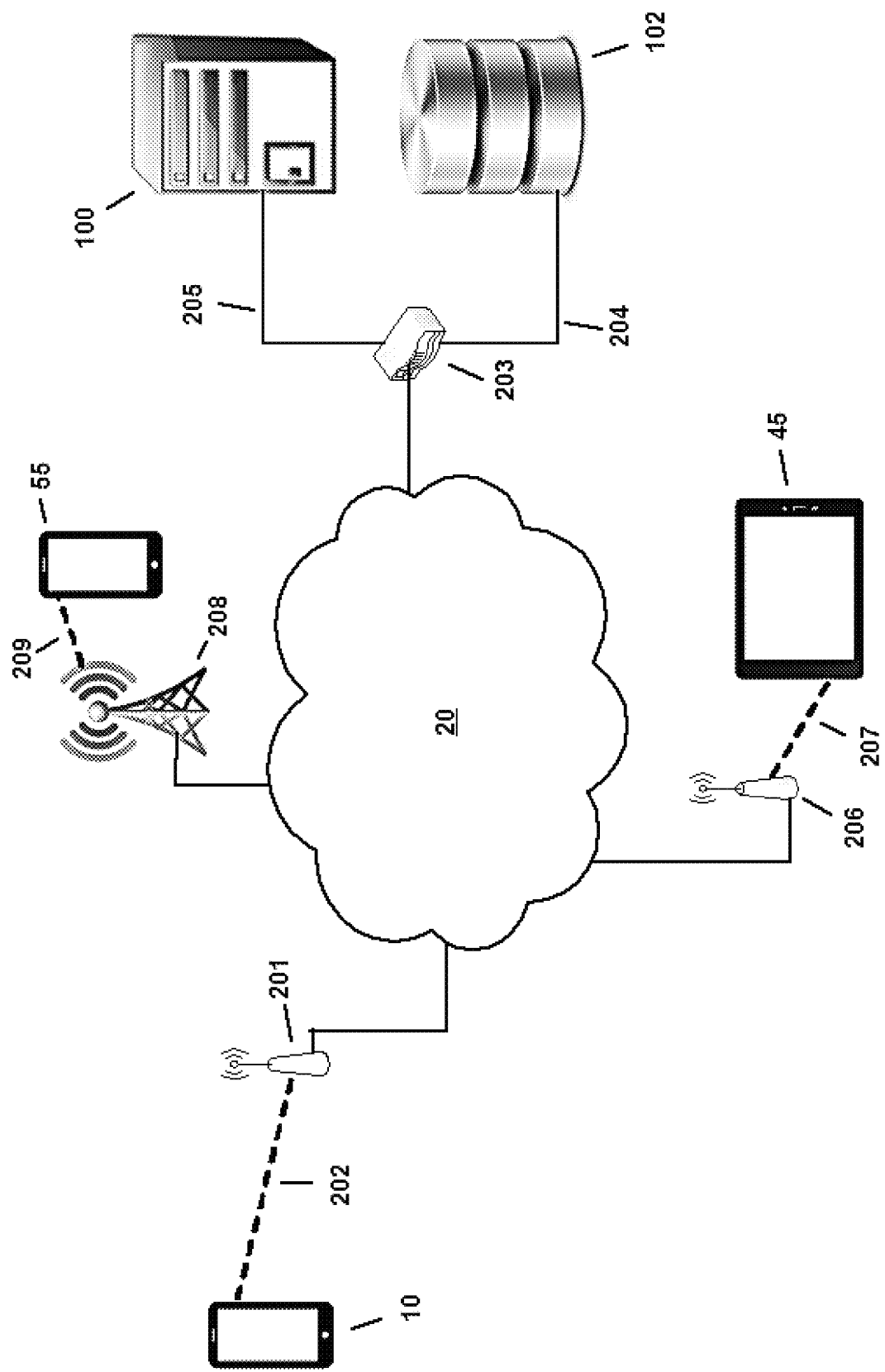
FIG. 2 depicts a schematic view of an exemplary health history access network configured to provide access to a user's health history based on receiving a patient health record, determining a relationship between the health record and the patient health history, determining a condition associated with the health record and the location on the patient's body affected by the condition, and automatically presenting the relationship between the health record and health history based on the condition.

FIG. 2 depicts a schematic view of an exemplary health history access network configured to provide access to a user's health history based on receiving a patient health record, determining a relationship between the health record and the patient health history, determining a condition associated with the health record and the location on the patient's body affected by the condition, and automatically presenting the relationship between the health record and health history based on the condition. In FIG. 2, according to an exemplary embodiment of the present disclosure, data may be transferred to the system, stored by the system, and/or transferred by the system to users of the system across local area networks (LANs) or wide area networks (WANs). In accordance with various embodiments, the system may include numerous servers, data mining hardware, computing devices, or any combination thereof, communicatively connected across one or more LANs and/or WANs. One of ordinary skill in the art would appreciate that there are numerous manners in which the system could be configured, and embodiments of the present disclosure are contemplated for use with any configuration. Referring to FIG. 2, a schematic overview of a system in accordance with an embodiment of the present disclosure is shown. In the depicted embodiment, the exemplary system includes the exemplary health history access system 100 configured to provide interactive access to health history adaptively presented on a visual patient anatomical model. In this example, the database 102 is a network attached storage computing device configured to provide access to retrievably storable patient health records and patient health history. In the illustrated embodiment, the mobile device 10 is a smartphone computing device configured to permit a medical patient to enter health record data for processing by the health history access system 100. In the depicted embodiment, the mobile device 45 is a tablet computing device configured to provide the medical patient's doctor interactive access to the patient's health history. In the depicted example, the mobile device 55 is a smartphone computing device configured to provide a medical professional new to the patient with access to the patient's health history. In the illustrated embodiment, the mobile device 10 is communicatively and operably coupled by the wireless access point 201 and the wireless link 202 with the network cloud 20 (for example, the Internet) to send, retrieve, or manipulate information in storage devices, servers, and network components, and exchange information with various other systems and devices via the network cloud 20. In the depicted example, the illustrative system includes the router 203 configured to communicatively and operably couple the database 102 to the network cloud 20 via the communication link 204. In the illustrated example, the router 203 also communicatively and operably couples the health history access system 100 to the network cloud 20 via the communication link 205. In the depicted embodiment, the mobile device 45 is communicatively and operably coupled with the network cloud 20 by the wireless access point 206 and the wireless communication link 207. In the illustrated embodiment, the mobile device 55 is communicatively and operably coupled with the network cloud 20 via the mobile data tower 208 through the wireless communication link 209. In various examples, one or more of: the mobile device 10, mobile device 45, mobile device 55, database 102, or health history access system 100 may include an application server configured to store or provide access to information used by the system. In various embodiments, one or more application server may retrieve or manipulate information in storage devices and exchange information through the network cloud 20. In some examples, one or more of: the mobile device 10, mobile device 45, mobile device 55, database 102, or health history access system 100 may include various applications implemented as processor-executable program instructions. In some embodiments, various processor-executable program instruction applications may also be used to manipulate information stored remotely and process and analyze data stored remotely across the network cloud 20 (for example, the Internet). According to an exemplary embodiment, as shown in FIG. 2, exchange of information through the network cloud 20 or other network may occur through one or more high speed connections. In some cases, high speed connections may be over-the-air (OTA), passed through networked systems, directly connected to one or more network cloud 20 or directed through one or more router. In various implementations, one or more router may be optional, and other embodiments in accordance with the present disclosure may or may not utilize one or more router. One of ordinary skill in the art would appreciate that there are numerous ways any or all of the depicted devices may connect with the network cloud 20 for the exchange of information, and embodiments of the present disclosure are contemplated for use with any method for connecting to networks for the purpose of exchanging information. Further, while this application may refer to high speed connections, embodiments of the present disclosure may be utilized with connections of any useful speed. In an illustrative example, components or modules of the system may connect to one or more of: the mobile device 10, mobile device 45, mobile device 55, database 102, or health history access system 100 via the network cloud 20 or other network in numerous ways. For instance, a component or module may connect to the system i) through a computing device directly connected to the network cloud 20, ii) through a computing device connected to the network cloud 20 through a routing device, or iii) through a computing device connected to a wireless access point. One of ordinary skill in the art will appreciate that there are numerous ways that a component or module may connect to a device via network cloud 20 or other network, and embodiments of the present disclosure are contemplated for use with any network connection method. In various examples, one or more of: the mobile device 10, mobile device 45, mobile device 55, database 102, or health history access system 100 could include an interface to a personal computing device, such as, for example, another smartphone, another tablet computer, a wearable computing device, a cloud-based computing device, a virtual computing device, or a desktop computing device, configured to operate as a host for other computing devices to connect to. In some examples, one or more communications means of the system may be any circuitry or other means for communicating data over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

Figure 3:
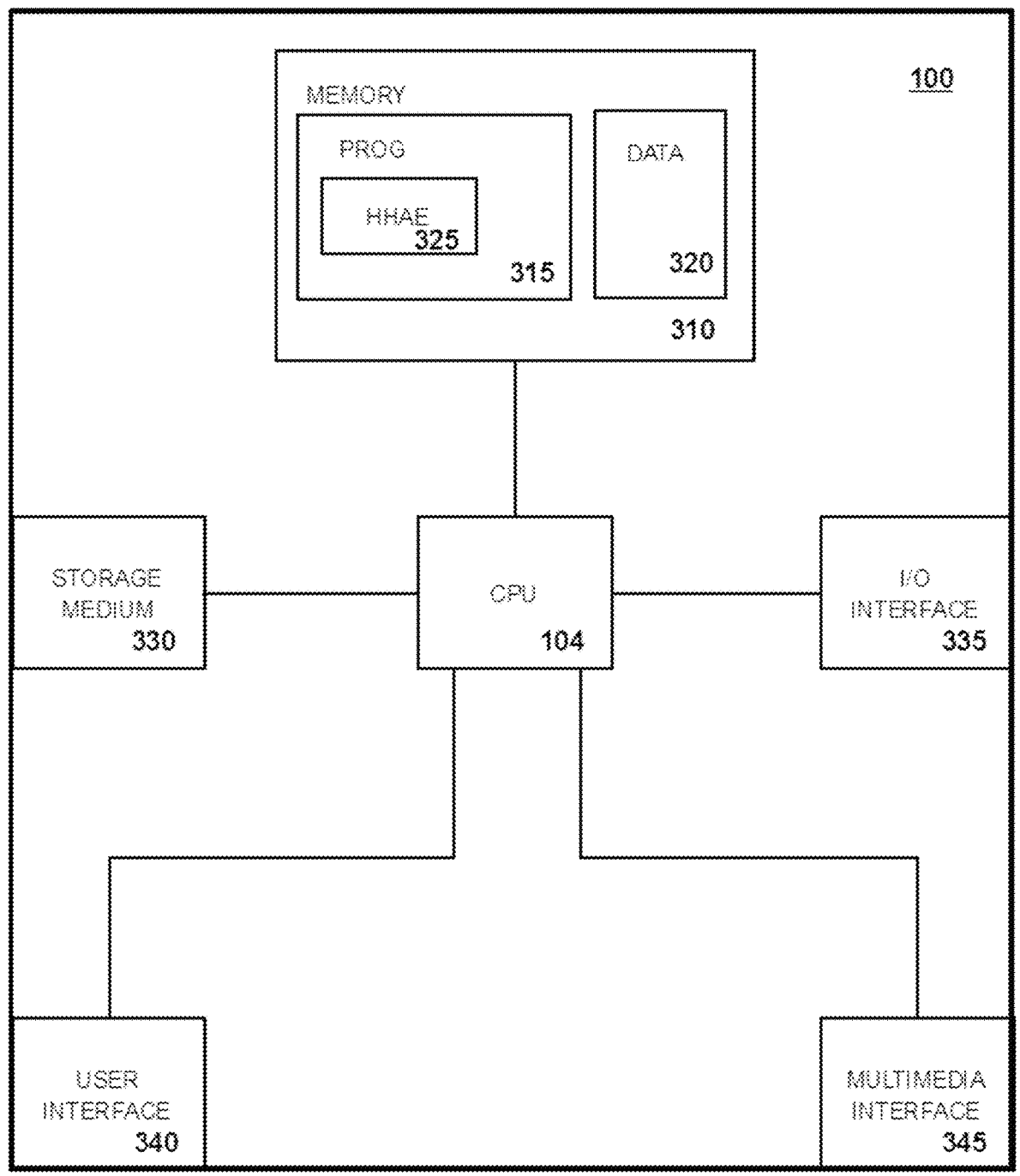
FIG. 3 depicts a structural view of an exemplary computing device configured with an exemplary Health History Access Engine (HHAE) to adapt the computing device to provide access to a user's health history based on receiving a patient health record, determining a relationship between the health record and the patient health history, determining a condition associated with the health record and the location on the patient's body affected by the condition, and automatically presenting the relationship between the health record and health history based on the condition.

FIG. 3 depicts a structural view of an exemplary computing device configured with an exemplary Health History Access Engine (HHAE) to adapt the computing device to provide access to a user's health history based on receiving a patient health record, determining a relationship between the health record and the patient health history, determining a condition associated with the health record and the location on the patient's body affected by the condition, and automatically presenting the relationship between the health record and health history based on the condition. In FIG. 3, the block diagram of the exemplary health history access system 100 includes the processor 104, depicted in FIG. 1B. The processor 104 is in electrical communication with the memory 310. The depicted memory 310 includes the program memory 315 and the data memory 320. The depicted program memory 315 includes processor-executable program instructions implementing the HHAE (Health History Access Engine) 325. In some embodiments, the illustrated program memory 315 may include processor-executable program instructions configured to implement an OS (Operating System). In various embodiments, the OS may include processor executable program instructions configured to implement various operations when executed by the processor 104. In some embodiments, the OS may be omitted. In some embodiments, the illustrated program memory 315 may include processor-executable program instructions configured to implement various Application Software. In various embodiments, the Application Software may include processor executable program instructions configured to implement various operations when executed by the processor 104. In some embodiments, the Application Software may be omitted. In the depicted embodiment, the processor 104 is communicatively and operably coupled with the storage medium 330. In the depicted embodiment, the processor 104 is communicatively and operably coupled with the I/O (Input/Output) interface 335. In the depicted embodiment, the I/O interface 335 includes a network interface. In various implementations, the network interface may be a wireless network interface. In some designs, the network interface may be a Wi-Fi interface. In some embodiments, the network interface may be a BLUETOOTH interface. In an illustrative example, the health history access system 100 may include more than one network interface. In some designs, the network interface may be a wireline interface. In some designs, the network interface may be omitted. In the depicted embodiment, the processor 104 is communicatively and operably coupled with the user interface 340. The user interface may include the display unit 106, depicted in FIG. 1B. In various implementations, the user interface 340 may be adapted to receive input from a user or send output to a user. In some embodiments, the user interface 340 may be adapted to an input-only or output-only user interface mode. In various implementations, the user interface 340 may include an imaging display. In some embodiments, the user interface 340 may include an audio interface. In some designs, the audio interface may include an audio input. In various designs, the audio interface may include an audio output. In some implementations, the user interface 340 may be touch-sensitive. In some designs, the health history access system 100 may include an accelerometer operably coupled with the processor 104. In various embodiments, the health history access system 100 may include a GPS module operably coupled with the processor 104. In an illustrative example, the health history access system 100 may include a magnetometer operably coupled with the processor 104. In some embodiments, the user interface 340 may include an input sensor array. In various implementations, the input sensor array may include one or more imaging sensor. In various designs, the input sensor array may include one or more audio transducer. In some implementations, the input sensor array may include a radio-frequency detector. In an illustrative example, the input sensor array may include an ultrasonic audio transducer. In some embodiments, the input sensor array may include image sensing subsystems or modules configurable by the processor 104 to be adapted to provide image input capability, image output capability, image sampling, spectral image analysis, correlation, autocorrelation, Fourier transforms, image buffering, or image filtering operations including adjusting frequency response and attenuation characteristics of spatial domain and frequency domain filters, image recognition, pattern recognition, or anomaly detection. In various implementations, the depicted memory 310 may contain processor executable program instruction modules configurable by the processor 104 to be adapted to provide image input capability, image output capability, image sampling, spectral image analysis, correlation, autocorrelation, Fourier transforms, image buffering, or image filtering operations including adjusting frequency response and attenuation characteristics of spatial domain and frequency domain filters, image recognition, pattern recognition, or anomaly detection. In some embodiments, the input sensor array may include audio sensing subsystems or modules configurable by the processor 104 to be adapted to provide audio input capability, audio output capability, audio sampling, spectral audio analysis, correlation, autocorrelation, Fourier transforms, audio buffering, or audio filtering operations including adjusting frequency response and attenuation characteristics of temporal domain and frequency domain filters, audio pattern recognition, or anomaly detection. In various implementations, the depicted memory 310 may contain processor executable program instruction modules configurable by the processor 104 to be adapted to provide audio input capability, audio output capability, audio sampling, spectral audio analysis, correlation, autocorrelation, Fourier transforms, audio buffering, or audio filtering operations including adjusting frequency response and attenuation characteristics of temporal domain and frequency domain filters, audio pattern recognition, or anomaly detection. In the depicted embodiment, the processor 104 is communicatively and operably coupled with the multimedia interface 345. In the illustrated embodiment, the multimedia interface 345 includes interfaces adapted to input and output of audio, video, and image data. In some embodiments, the multimedia interface 345 may include one or more still image camera or video camera. In various designs, the multimedia interface 345 may include one or more microphone. In some implementations, the multimedia interface 345 may include a wireless communication means configured to operably and communicatively couple the multimedia interface 345 with a multimedia data source or sink external to the health history access system 100. In various designs, the multimedia interface 345 may include interfaces adapted to send, receive, or process encoded audio or video. In various embodiments, the multimedia interface 345 may include one or more video, image, or audio encoder. In various designs, the multimedia interface 345 may include one or more video, image, or audio decoder. In various implementations, the multimedia interface 345 may include interfaces adapted to send, receive, or process one or more multimedia stream. In various implementations, the multimedia interface 345 may include a GPU. In some embodiments, the multimedia interface 345 may be omitted. Useful examples of the illustrated health history access system 100 include, but are not limited to, personal computers, servers, tablet PCs, smartphones, or other computing devices. In some embodiments, multiple health history access system 100 devices may be operably linked to form a computer network in a manner as to distribute and share one or more resources, such as clustered computing devices and server banks/farms. Various examples of such general-purpose multi-unit computer networks suitable for embodiments of the disclosure, their typical configuration and many standardized communication links are well known to one skilled in the art, as explained in more detail in the foregoing FIG. 2 description. In some embodiments, an exemplary health history access system 100 design may be realized in a distributed implementation. In an illustrative example, some health history access system 100 designs may be partitioned between a client device, such as, for example, a phone, and, a more powerful server system, as depicted, for example, in FIG. 2. In various designs, a health history access system 100 partition hosted on a PC or mobile device may choose to delegate some parts of computation, such as, for example, machine learning or deep learning, to a host server. In some embodiments, a client device partition may delegate computation-intensive tasks to a host server to take advantage of a more powerful processor, or to offload excess work. In an illustrative example, some devices may be configured with a mobile chip including an engine adapted to implement specialized processing, such as, for example, neural networks, machine learning, artificial intelligence, image recognition, audio processing, or digital signal processing. In some embodiments, such an engine adapted to specialized processing may have sufficient processing power to implement some features. However, in some embodiments, an exemplary health history access system 100 may be configured to operate on a device with less processing power, such as, for example, various gaming consoles, which may not have sufficient processor power, or a suitable CPU architecture, to adequately support health history access system 100. Various embodiment designs configured to operate on a such a device with reduced processor power may work in conjunction with a more powerful server system.

Figure 4B:
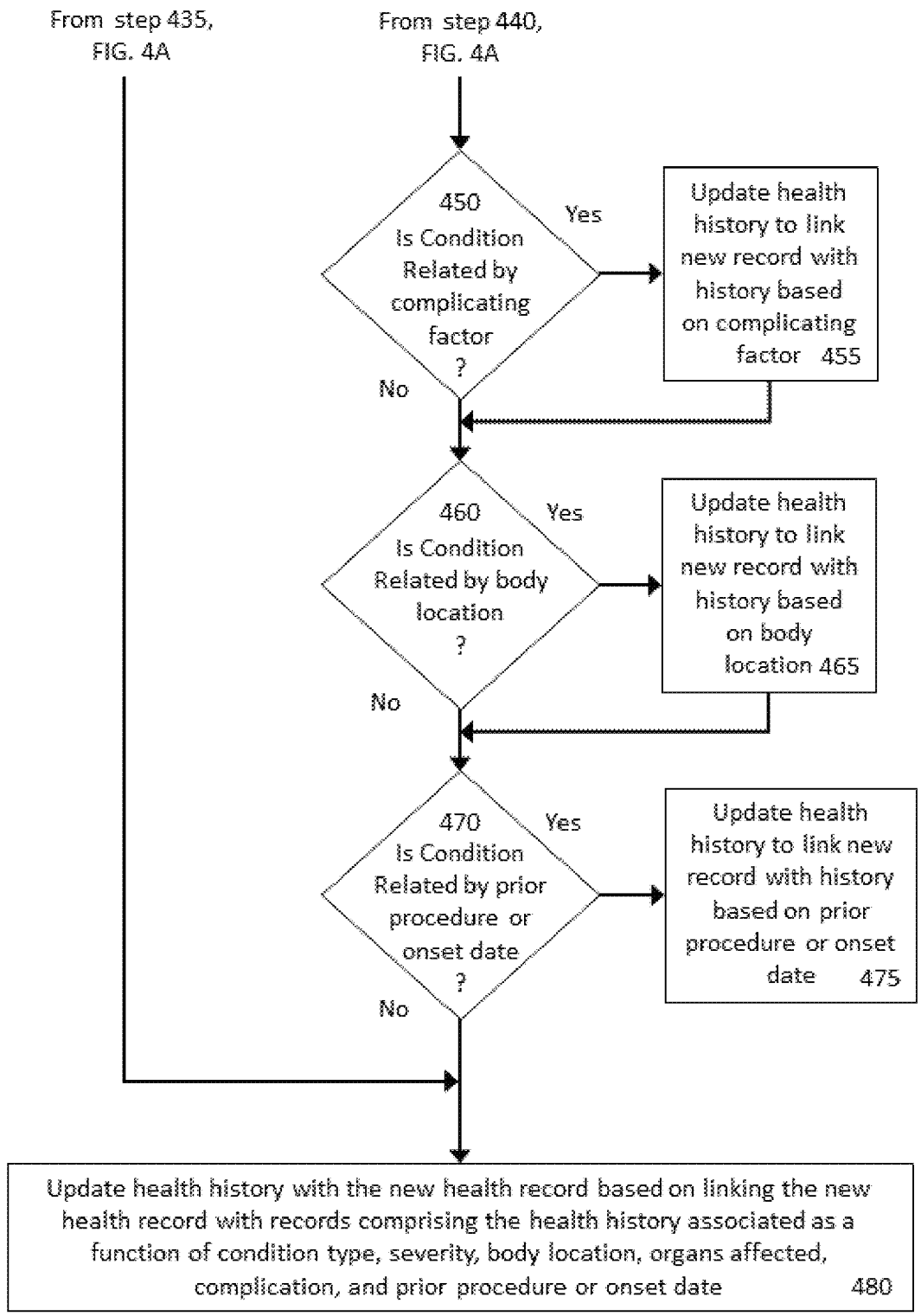

FIGS. 4A-4B together depict a process flow of an exemplary Health History Access Engine (HHAE) providing access to a user's health history in an exemplary health history comprehension mode driven by health record ingest. The method depicted in FIGS. 4A-4B is given from the perspective of the HHAE 325 implemented via processor-executable program instructions executing on the health history access system 100 processor 104, depicted at least in FIG. 1B and FIG. 3. In various embodiments, the method depicted in FIGS. 4A-4B may also be understood as from the perspective of processor-executable program instructions executing on a processor configured in any of the mobile device 10, mobile device 45, mobile device 55, or database 102, depicted at least in FIG. 2. In the illustrated embodiment, the HHAE 325 executes as program instructions on the processor 104 configured in the HHAE 325 host health history access system 100, depicted in at least FIG. 1A, FIG. 1B, FIG. 2, and FIG. 3. In some embodiments, the HHAE 325 may execute as a cloud service communicatively and operatively coupled with system services, hardware resources, or software elements local to and/or external to the HHAE 325 host health history access system 100.

The depicted method 400 begins at step 405 illustrated in FIG. 4A, with the processor 104 determining the type, severity, body location, affected organs, and prior procedure or onset date of the medical condition associated with a received health record, based on patient health information encoded by health record data fields.

Then, the method continues at step 410 with the processor 104 performing a test to determine if the medical condition associated with the health record received by the processor 104 at step 405 is systemic, based on the health record data fields. The processor 104 may determine if the condition indicated by the health record is systemic based on comparing the health record condition type data with predetermined diagnosis or condition data representative of possible diagnoses or possible conditions. Upon a determination by the processor 104 at step 410 the condition is systemic, the method continues at step 415 with the processor 104 flagging the condition as systemic, and the method continues at step 420.

Upon a determination by the processor 104 at step 410 the condition is not systemic, the method continues at step 420 with the processor 104 performing a test to determine if the condition is severe, based on the health record data fields. The processor 104 may determine if the condition indicated by the health record is severe based on comparing the health record condition severity data with predetermined diagnosis or condition data representative of possible diagnoses or possible conditions. Upon a determination by the processor 104 at step 420 the condition is severe, the method continues at step 425 with the processor 104 flagging the condition as severe, and the method continues at step 430.

Upon a determination by the processor 104 at step 420 the condition is not severe, the method continues at step 430 with the processor 104 comparing the condition type, severity, organs affected, complicating factors, body location, prior procedures, and onset date data encoded by the received health record with patient health history, to determine if the medical condition is related to one or more health record comprising the health history, based on the comparison. The health history may be a collection of health records previously linked by the processor 104 based on comparing the health record data fields encoding condition type, severity, organs affected, complicating factors, body location, prior procedures, and onset date data encoded by the health record with patient health history. In an illustrative example, each health record of the linked health records comprising the health history may include multiple data fields encoding patient health information, such as, for example, condition name, condition type (for example, systemic or non-systemic), organs affected, body location, onset date, procedure name, diagnosis name, diagnosis code, diagnosis type (for example, pertinent positive, pertinent negative), condition severity (for example, critical, severe, moderate, mild), or condition status (for example, unmanaged, managed, ongoing, recovering, recovered).

Then, the method continues at step 435 with the processor 104 performing a test, to determine if the condition indicated by the received health record is related to the health history. The processor 104 may determine if the health record is related to the health history based on comparing data encoded by the patient health information data encoded by the received health record data fields with data encoded by the linked health records forming the health history, and predetermined conditions data representative of conditions and related conditions. For example, predetermined related conditions data may indicate high blood pressure levels are related as a complicating factor in combination with high cholesterol levels. A received health record indicating high blood pressure may be determined by the processor 104 as related to the patient health history if high cholesterol were indicated by a health record previously comprehended by the processor 104 and linked with other previously ingested health records to form the health history. Other relationships between medical conditions may be determined by the processor 104 based on comparing health record data fields encoding condition type, severity, organs affected, complicating factors, body location, prior procedures, and onset data encoded by the health records. The processor 104 may perform multiple operations between all or a portion of the health records and health history to determine if a condition is related to the health history. In an illustrative example, the processor 104 may determine a condition is related to another condition by multiple interdependent factors medically relating the condition to another condition encoded by the linked health records comprising the health history. The processor 104 may determine a condition is related to multiple conditions, using logic similar to what has been described with reference to relating conditions based on interdependent factors.

Upon a determination by the processor 104 at step 435 the condition indicated by the received health record is not related to the health history, the method continues at step 480, illustrated in FIG. 4B. Upon a determination by the processor 104 at step 435 the condition indicated by the received health record is related to the health history, the method continues at step 440 with the processor 104 performing a test to determine if the condition indicated by the received health record is related to the health history by organs affected. Upon a determination by the processor 104 at step 440 the condition indicated by the received health record is related to the health history by organs affected, the method continues at step 445 with the processor 104 updating the health history to link the new received health record with the patient health history based on organs affected, and the method continues at step 450, illustrated in FIG. 4B.

Upon a determination by the processor 104 at step 440 the condition indicated by the received health record is not related to the health history by organs affected, the method continues at step 450, illustrated in FIG. 4B, with the processor 104 performing a test to determine if the condition indicated by the received health record is related to the patient health history by a complicating factor. Upon a determination by the processor 104 at step 450 the condition indicated by the received health record is related to the patient health history by a complicating factor, the method continues at step 455 with the processor 104 updating the patient health history to link the new received health record with the patient health history based on complicating factor, and the method continues at step 460.

Upon a determination by the processor 104 at step 450 the condition indicated by the received health record is not related to the patient health history by a complicating factor, the method continues at step 460 with the processor 104 performing a test to determine if the condition indicated by the received health record is related to the patient health history by body location. Upon a determination by the processor 104 at step 460 the received health record is related to the patient health history by body location, the method continues at step 465 with the processor 104 updating the patient health history to link the new received health record with the patient health history based on body location, and the method continues at step 470.

Upon a determination by the processor 104 at step 460 the received health record is not related to the patient health history by body location, the method continues at step 470 with the processor 104 performing a test to determine if the condition indicated by the received health record is related to the patient health history based on prior procedure type or onset date. Upon a determination by the processor 104 at step 470 the received health record is related to the patient health history based on prior procedure or onset date, the method continues at step 475 with the processor 104 updating the patient health history to link the new received health record with the patient health history based on prior procedure or onset date. The method 400 may continue at step 405. The method 400 may end.

Upon a determination by the processor 104 at step 470 the received health record is not related to the patient health history based on prior procedure or onset date, the method continues at step 480 with the processor 104 updating the patient health history with the new received health record based on linking the new health record with the linked health records comprising the patient health history associated as a function of condition type, severity, body location, organs affected, complication, and prior procedure or onset date. The method 400 may continue at step 405. The method 400 may end.

Figure 5A:
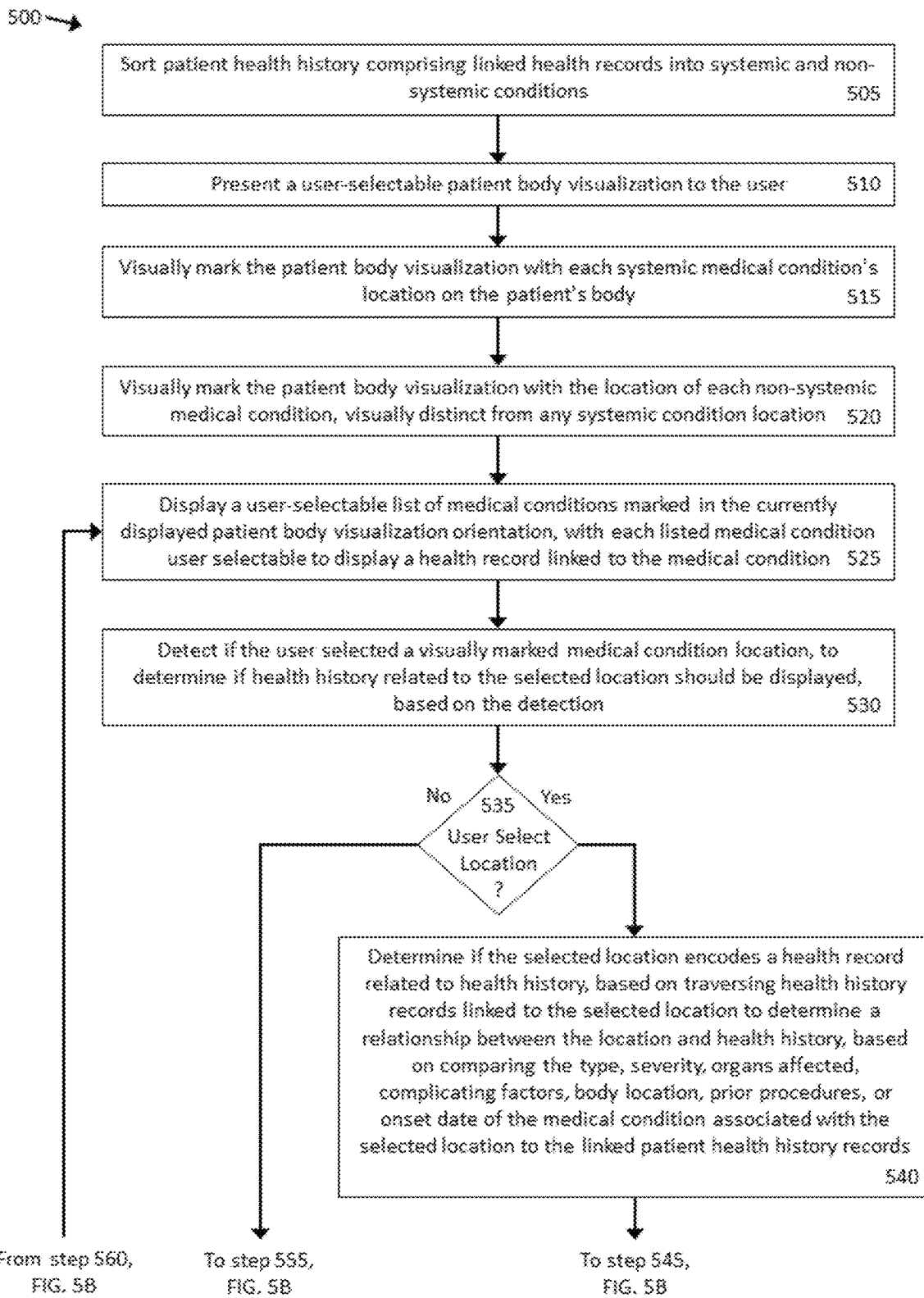
FIGS. 5A-5B together depict a process flow of an exemplary Health History Access Engine (HHAE) providing access to a user's health history in an exemplary interactive health history presentation mode driven by user navigation input.
Figure 5B:
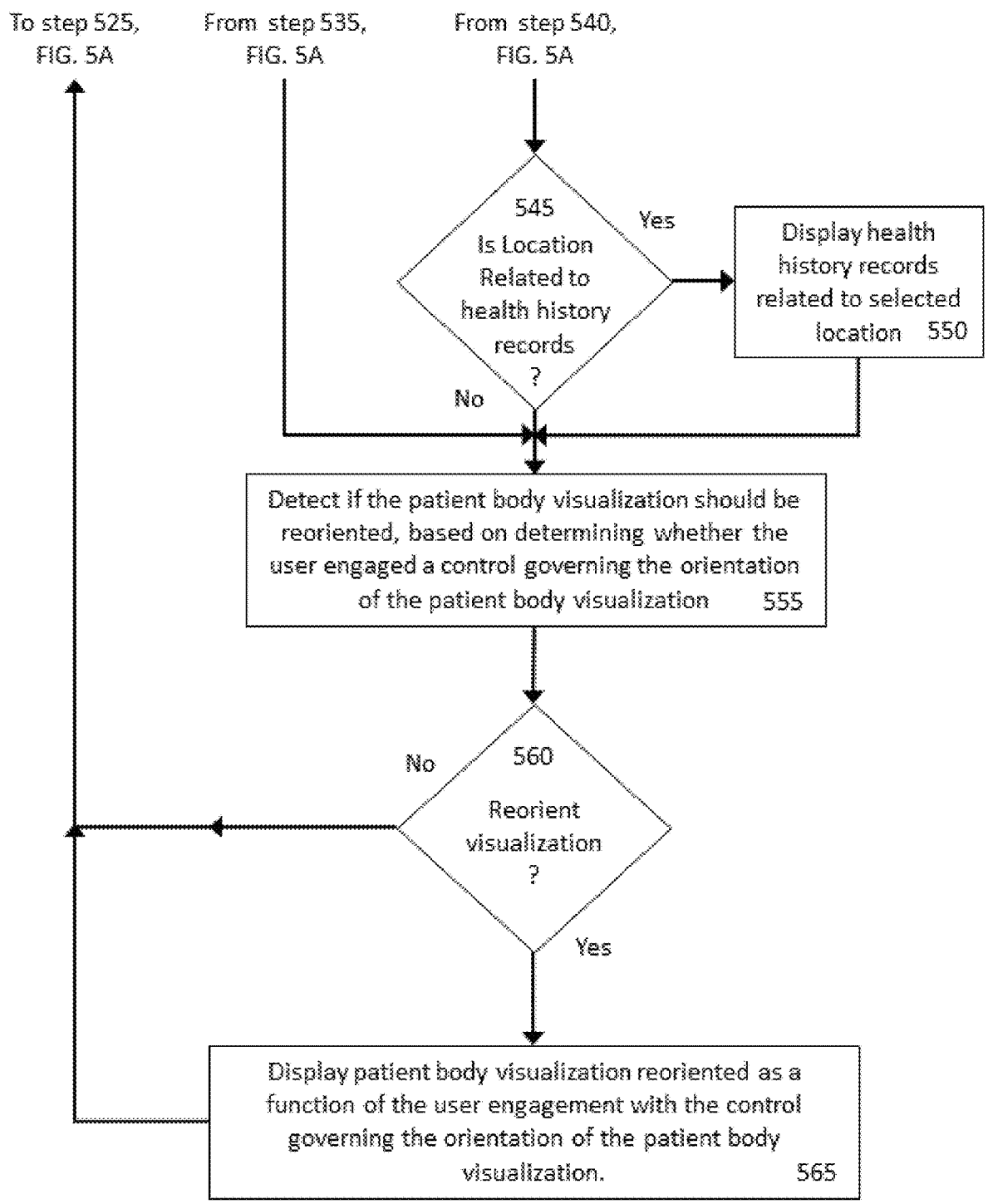

FIGS. 5A-5B together depict a process flow of an exemplary Health History Access Engine (HHAE) providing access to a user's health history in an exemplary interactive health history presentation mode driven by user navigation input. The method depicted in FIGS. 5A-5B is given from the perspective of the HHAE 325 implemented via processor-executable program instructions executing on the health history access system 100 processor 104, depicted at least in FIG. 1B and FIG. 3. In various embodiments, the method depicted in FIGS. 5A-5B may also be understood as from the perspective of processor-executable program instructions executing on a processor configured in any of the mobile device 10, mobile device 45, mobile device 55, or database 102, depicted at least in FIG. 2. In the illustrated embodiment, the HHAE 325 executes as program instructions on the processor 104 configured in the HHAE 325 host health history access system 100, depicted in at least FIG. 1A, FIG. 1B, FIG. 2, and FIG. 3. In some embodiments, the HHAE 325 may execute as a cloud service communicatively and operatively coupled with system services, hardware resources, or software elements local to and/or external to the HHAE 325 host health history access system 100. The depicted method 500 begins at step 505 illustrated in FIG. 5A, with the processor 104 sorting patient health history comprising linked heath records into systemic and non-systemic conditions.

Then, method continues at step 510 with the processor 104 presenting a user selectable patient body visualization to the user.

Then, the method continues at step 515 with the processor 104 visually marking the patient body visualization with each systemic medical condition's location on the patient's body.

Then, the method continues at step 520 with the processor 104 visually marking the patient body visualization with the location of each non-systemic medical condition, visually distinct from any systemic condition location.

Then, the method continues at step 525 with the processor 104 displaying a user selectable list of medical conditions marked in the currently displayed patient body visualization orientation, with each listed medical condition user selectable to display when selected a health record linked to the medical condition. User selection may be based on a user interface click, tap, drag, gesture, or other similar user interaction with the user interface. The user interface may be configured to detect human visible or human invisible light energy incident to various locations on the user interface screen or other input surface. User selection may be based on the processor 104 determining the light energy incident to various user interface locations as a function of time. In an illustrative example, user selection and navigation may be based on a user employing a laser pointer to navigate the patient body visualization.

Then, the method continues at step 530 with the processor 104 detecting if the user selected a visually marked medical condition body location, to determine if health history related to the selected location should be displayed, based on the detection.

Then, the method continues at step 535 with the processor 104 performing a test to determine if the user selected a location, based on the detection performed by the processor 104 at step 530. Upon a determination by the processor 104 at step 535 the user did not select a visually marked medical condition body location, the method continues at step 555 illustrated in FIG. 5B.

Upon a determination by the processor 104 at step 535 the user did select a visually marked medical condition body location, the method continues at step 540 with the processor 104 determining if the selected location encodes a health record related to the health history, based on traversing linked health history records to determine a relationship between the location and health history, based on comparing the type, severity, organs affected, complicating factors, body location, prior procedures, or onset date of the medical condition associated with the selected location to the linked patient health history records. The processor 104 may traverse health history records linked to the selected location before health history records not linked to the selected location, to determine more quickly in some cases if a relationship between the health record, the health history, and the location exists.

Then, the method continues at step 545 illustrated in FIG. 5B, with the processor 104 performing a test to determine if the selected location is related to patient health history, based on the determination by the processor 104 at step 540. Upon a determination by the processor 104 at step 545 the location is related to the patient health history, the method continues at step 550 with the processor 104 displaying the health history records related to the selected location, and the method continues at step 555.

At step 555, the processor 104 detects if the patient body visualization should be reoriented, based on determining whether the user engaged a control governing the orientation of the patient body visualization.

Then, the method continues at step 560 with the processor 104 performing a test to determine if the patient body visualization should be reoriented, based on the detection performed by the processor 104 at step 555. Upon a determination by the processor 104 at step 560 the patient body visualization should not be reoriented, the method continues at step 525 illustrated in FIG. 5A, with the processor 104 displaying a user selectable list of medical conditions marked in the currently displayed patient body visualization orientation, with each listed medical condition user selectable to display when selected a health record linked to the medical condition.

Upon a determination by the processor 104 at step 560 the patient body visualization should be reoriented, the method continues at step 565 with the processor 104 displaying the patient body visualization reoriented as a function of the user engagement with the control governing the orientation of the patient body visualization. The method 500 may end. The method 500 may continue at step 505.

FIGS. 6A-6C together depict illustrative examples of health history based on associated health record data. In FIG. 6A, the exemplary unlinked collection of health records 605, 610, 615, 620, 625, and 630 include patient data fields encoding exemplary health record data including type, description, date, category, and status. The health record type may be, for example, Condition, Procedure, Diagnosis, Life Event, and the like. The Condition type may include the condition name. Other health record data in various formats may be encoded to facilitate health history linkage, as one of ordinary skill would recognize. Multiple such health records may be linked to form a health history, based on associating the health record patient data fields between more than one health record. No particular implementation of health record linking should be assumed from the FIGS. 6A-6C examples. For example, records may be associated through a linked list, tree, or the like. Hash functions and hash tables may be employed to classify or aggregate records of various types. For example, a Bloom filter may be configured to quickly determine if a record having a secondary type may exist in a collection hashed by primary type. Many techniques to link records may be employed by various embodiments, as the skilled artisan would recognize. Multiple aspects of health history may be formed from an unlinked health record collection. For example, a health history timeline may link health records in date order. A systemic health history may link health records marked as systemic. A systemic health history may include a health record indicating a non-systemic condition as a complicating factor to a systemic condition. A condition severity health history may link conditions in descending order of condition severity. Other associations are possible, as the skilled artisan would recognize, to form a health history constructed from linked health records. In the depicted example, health record 605 encodes Type: Condition, Description: High Blood Pressure, Date: 2015, Category: Systemic, and Status: Moderate, Ongoing. In the depicted example, health record 610 encodes Type: Procedure, Description: Tonsillectomy, Date: 1992, Category: Non-systemic, and Status: Not Severe. In the depicted example, health record 615 encodes Type: Procedure, Diagnosis: Aortic Arch Replacement, Date: 2017, Category: Systemic, and Status: Critical. In the depicted example, health record 620 encodes Type: Medication, Description: Blood Pressure Medication, Date: 2015, Category: Systemic, and Status: Critical, Ongoing. In the depicted example, health record 625 encodes Type: Condition, Diagnosis: Deep Vein Thrombosis, Date: 2019, Category: Systemic, and Status: Critical, Recovered. In the depicted example, health record 630 encodes Type: Injury, Diagnosis: Broken Wrist, Date: 1998, Category: Non-systemic, and Status: Not Severe, Recovered.

In FIG. 6B, the systemic health history formed by linked health records 625, 605, 615, and 620 is displayed as the systemic aspect 65 of the health history model 25, including the chest 30 and the leg 35. The user may access the depicted health history formed by linked health records 625, 605, 615, and 620 by selecting the chest 30 location, or the leg location 35. The chest 30 location is related to the systemic health record 615, Aortic Arch Replacement. The leg 35 location is related to the systemic health record 625, Deep Vein Thrombosis. The user may navigate the health history model by clicking on a patient body location visibly marked on the health history model 25. The user may navigate the health history records presented in the user selectable health record list 85.

In FIG. 6C, the systemic and non-systemic health history formed by linked health records 610, 630, 625, 605, and 615 is displayed as the standard aspect 70 of the health history model 25, including the wrist 75, the chest 30, and the leg 35. The user may access the depicted health history formed by linked health records 610, 630, 625, 605, and 615 by selecting the wrist 75 location, the chest 30 location, or the leg location 35. The systemic condition locations 30 and 35 are marked visually distinct from the non-systemic condition location 75. The chest 30 location is related to the systemic health record 615, Aortic Arch Replacement. The leg 35 location is related to the systemic health record 625, Deep Vein Thrombosis. The user may navigate the health history model by clicking on a patient body location visibly marked on the health history model 25. The user may navigate the health history records presented in the user selectable health record list 85.

FIGS. 7A-7J together depict various views of exemplary health record input scenarios.

Figure 7A:
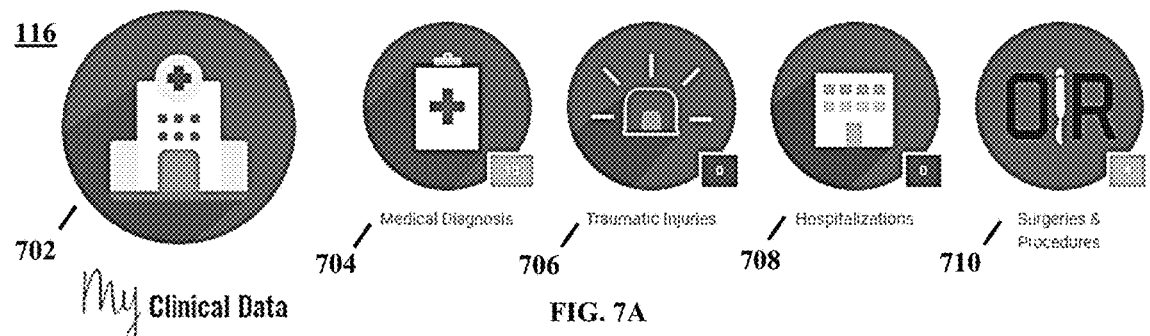

FIG. 7A is a screenshot illustrating an exemplary historical health data module 116 clinical data section 702 configured to receive a patient's clinical data. Non-limiting examples of the clinical data include Medical Diagnosis 704, Traumatic Injuries 706, Hospitalizations 708, and Surgeries & Procedures 710. The clinical data section 702 is configured to provide user options to search for and enter health record data through the Medical Diagnosis 704, Traumatic Injuries 706, Hospitalizations 708, and Surgeries & Procedures 710 interfaces. The clinical data section 702 may be configured to provide user options to add life events.

Figure 7B:
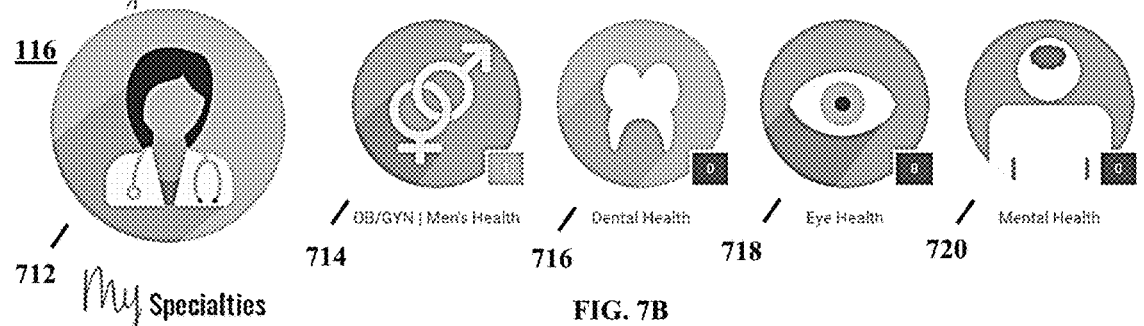

FIG. 7B is a screenshot illustrating an exemplary historical health data module 116 specialties data section 712 configured to receive a patient's medical specialties data. Non-limiting examples of the medical specialties data include OB/GYN—Men's Health 714, Dental Health 716, Eye Health 718, and Mental Health 720. The specialties data section 712 is configured to provide user options to search for and enter health record data through the OB/GYN—Men's Health 714, Dental Health 716, Eye Health 718, and Mental Health 720 interfaces. The specialties data section 712 may be configured to provide user options to add life events.

Figure 7C:
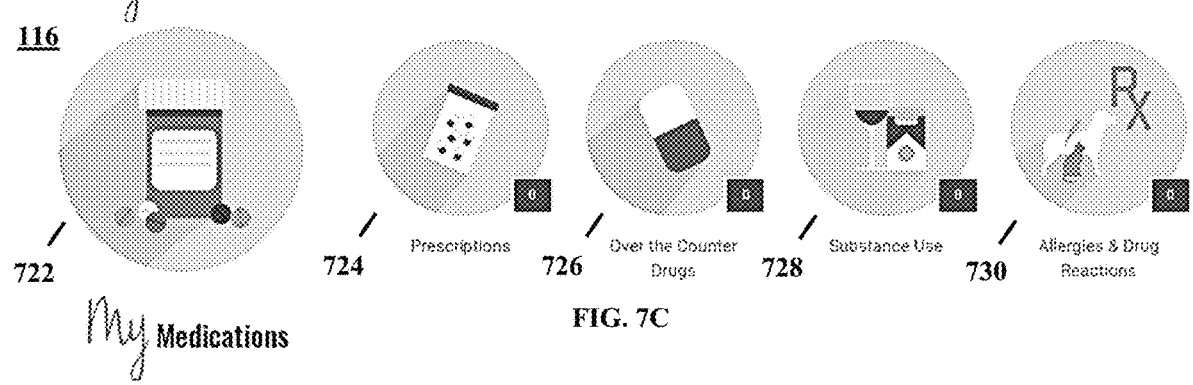

FIG. 7C is a screenshot illustrating an exemplary historical health data module 116 medication data section 722 configured to receive a patient's medication data. Non-limiting examples of the medication data include prescriptions 724, over the counter drugs 726, substance use 728, and allergies & drug interactions 730. In an illustrative example, the over the counter drugs 726 data may include nutrition supplements, or vitamins. The medication data section 722 is configured to provide user options to search for and enter health record data through the prescriptions 724, over the counter drugs 726, substance use 728, and allergies & drug interactions 730 interfaces. The medication data section 722 may be configured to provide user options to add life events.

Figure 7D:
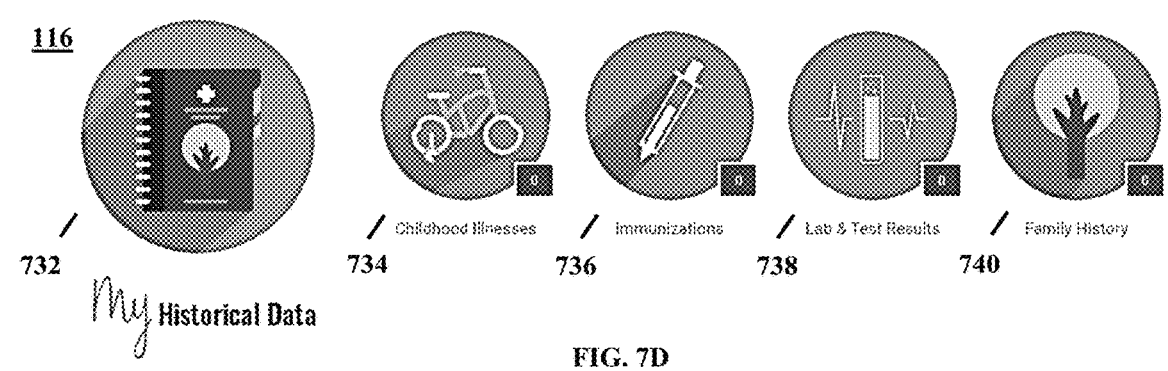

FIG. 7D is a screenshot illustrating an exemplary historical health data module 116 historical data section 732 configured to receive a patient's historical data. Non-limiting examples of the historical data include childhood illnesses 734, immunizations 736, lab & test results 738, and family history 740. The historical data section 732 is configured to provide user options to search for and enter health record data through the childhood illnesses 734, immunizations 736, lab & test results 738, and family history 740 interfaces. The historical data section 732 may be configured to provide user options to add life events.

Figure 7E:
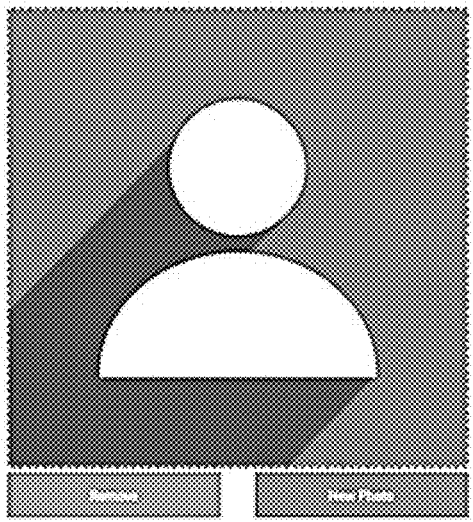

FIG. 7E is a screenshot depicting an exemplary patient registration module 110 configured to receive personal information of patients. Non-limiting examples of personal information include date of birth, gender, ethnicity, religion, preferred units (feet, pounds, meters, and the like), height, weight, waist size, BMI (automatically calculated on receiving above details), blood type, and the like. In an illustrative example, the database may receive an email address and a password to provide access to the plurality of modules. The patient registration module 110 may run a wizard protocol which walks the patient through each step to help in the registration process.

Figure 7F:
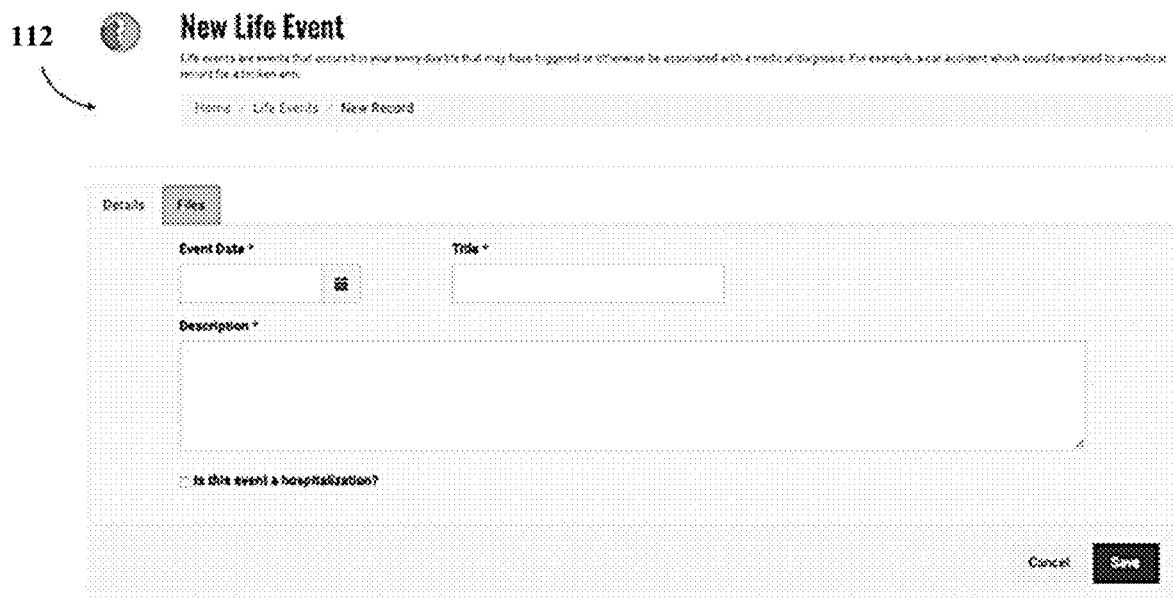

FIG. 7F is a screenshot depicting an exemplary life event module 112 configured to receive a patient's life event details related to health issues. Non-limiting examples of the life event details include event date, title, description, whether event resulted in hospitalization, and the like. In an illustrative example, the life events may then be mapped on the 3-D visualization output by the date and title given to the life event. The life event module 112 may be configured to allow categorization of the life event. Non-limiting examples of the life event include a house fire, divorce, had children, death in the family, and the like. This facilitation allows the user to check health issues that may have occurred at the particular life event. The life event module 112 may run a wizard protocol which walks the patient through each step of the process to help in adding the life event.

Figure 7G:

FIG. 7G is a screenshot depicting an exemplary healthcare professional module 114 configured to receive a patient's healthcare professional information. Non-limiting examples of the professional information include specialty, name, street address, suite, phone number, email address, website address, city, state, zip, country, and the like. The healthcare professional information may aid contacting the relevant healthcare professional. Non-limiting examples of the healthcare professional include patient's general practitioner, specialists, nutritionists, home healthcare providers, or anyone that they see in relation to their health care. These professionals may also be chosen by the user to connect with a specific health diagnosis or procedure. For example, if they had their wisdom teeth removed, the information of the oral surgeon who performed this procedure may be added to the healthcare professional module 114.

Figure 7H:

FIG. 7H is a screenshot depicting an exemplary medical diagnosis health record input interface 742 configured to permit user entry of medical diagnosis health record data. In the depicted example, the user may input a medical diagnosis in the diagnosis search/entry 744*a* box. The user may type a few starting characters of a diagnosis name into the diagnosis search/entry 744*a* box, for immediate search for a diagnosis with a name matching the first few characters entered. The user may also configure the event date 744*b*, related life event 744*c*, and diagnosing professional 744*d* in the medical diagnosis health record input interface 742. In the depicted example, the user may input the body location affected by the condition related to this record. The affected body location is specified from the point of view of the patient, in relation to the patient's body, by the general body location 744*e* (in this example, Thorax), Front or Back 744*f* (in this example, Front), and Left or Right 744*g* (in this example, Both/Center). The user my designate the pertinence of the diagnosis related to this record using the Pertinence selector 744*h* to designate Pertinence Negative or Pertinence Positive (in this example, Positive). In the depicted example, the user may enter a diagnosis description into the Details 744*i* box. The user may enter prescription information into the Prescription 744*j* box.

Figure 7I:

FIG. 7I is a screenshot depicting an exemplary traumatic injury health record input interface 744 configured to permit user entry of traumatic injury health record data. In the depicted example, the user may input a traumatic injury in the search/entry 746*a* box. The user may type a few starting characters of an injury name into the search/entry 746*a* box, for immediate search for an injury with a name matching the first few characters entered. The user may also configure the event date 746*b*, related life event 746*c*, and diagnosing professional 746*d* in the medical diagnosis health record input interface 744. In the depicted example, the user may input the body location affected by the condition related to this record. The affected body location is specified from the point of view of the patient, in relation to the patient's body, by the general body location 744*e* using the exemplary drop-down list; Front or Back 744*f* using the exemplary drop-down list; and Left or Right 744*g* using the exemplary drop-down list. The user my designate the pertinence of the diagnosis related to this record using the Pertinence selector 744*h* to designate Pertinence Negative or Pertinence Positive. In the depicted example, the user may enter a description into the Details 746*f* box. The user may enter prescription information into the Prescription 746*g* box.

FIG. 7J is a screenshot depicting an exemplary hospitalization health record input interface 748 configured to permit user entry of hospitalization health record data. In the depicted example, the user may input a diagnosis related to a hospitalization in the search/entry 750*a* box. The user may type a few starting characters of a diagnosis name into the search/entry 750*a* box, for immediate search for a diagnosis with a name matching the first few characters entered. The user may also configure the event date 750*b*, related life event 750*c*, and diagnosing professional 750*d* in the hospitalization health record input interface 745. In the depicted example, the user may input the body location affected by the condition related to this record. The affected body location is specified from the point of view of the patient, in relation to the patient's body, by the general body location 744*e* using the exemplary drop-down list 750*h*; Front or Back 744*f*; and Left or Right 744*g*. The user may designate the pertinence of the diagnosis related to this record using the Pertinence selector 744*h* to designate Pertinence Negative or Pertinence Positive. In the depicted example, the user may enter a description into the Details 750*f* box. The user may enter prescription information into the Prescription 750*g* box.

FIGS. 8A-8D together depict various views of exemplary health history presentation.

Figure 8A:
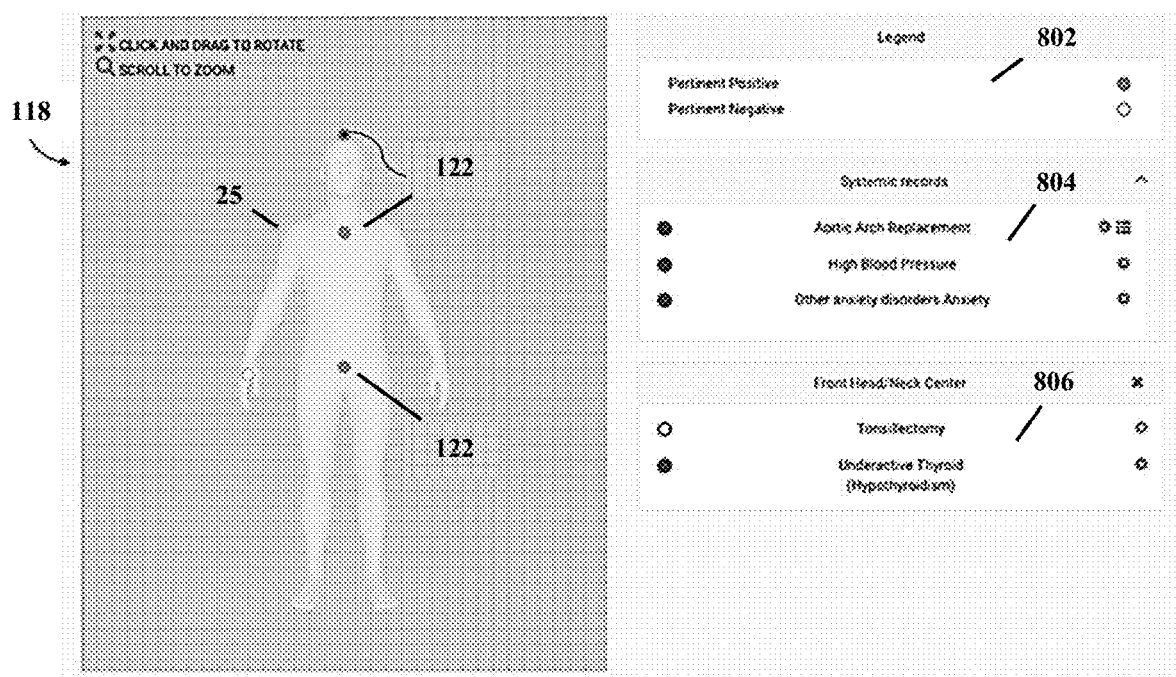
FIGS. 8A-8D together depict various views of exemplary health history presentation.

FIG. 8A is a screenshot depicting an exemplary visual mapping module 118 configured to provide a 3-D visual output of the patient's anatomy with the patient's health data and life event details. The depicted three-dimensional patient's anatomy includes the health history model 25, depicted at least in FIG. 1A, FIG. 6B, and FIG. 6C. The depicted three-dimensional patient's anatomy may be manipulated by zooming in and out and rotating 360 degrees to provide an overview of the user's health history. The visual mapping module 118 displays indicators 122 on the 3-D visual output patient's anatomy. The user is able to view the specific mapped diagnosis by clicking on indicators 122 automated by the data on the anatomy. The depicted visual mapping module 118 display includes the pertinence indication 802 (positive or negative), systemic records 804 and user-selected records 806. The depicted example systemic records 804 include Aortic Arch Replacement, High Blood Pressure, and Anxiety. The depicted example user-selected records 806 include a Tonsillectomy, and a Thyroid condition, associated with the Front Head/Neck Center body location selected in the user interface. The visual output allows the healthcare provider to quickly understand the patient's history and related health issues and thus spend more time in patient care.

Figure 8B:
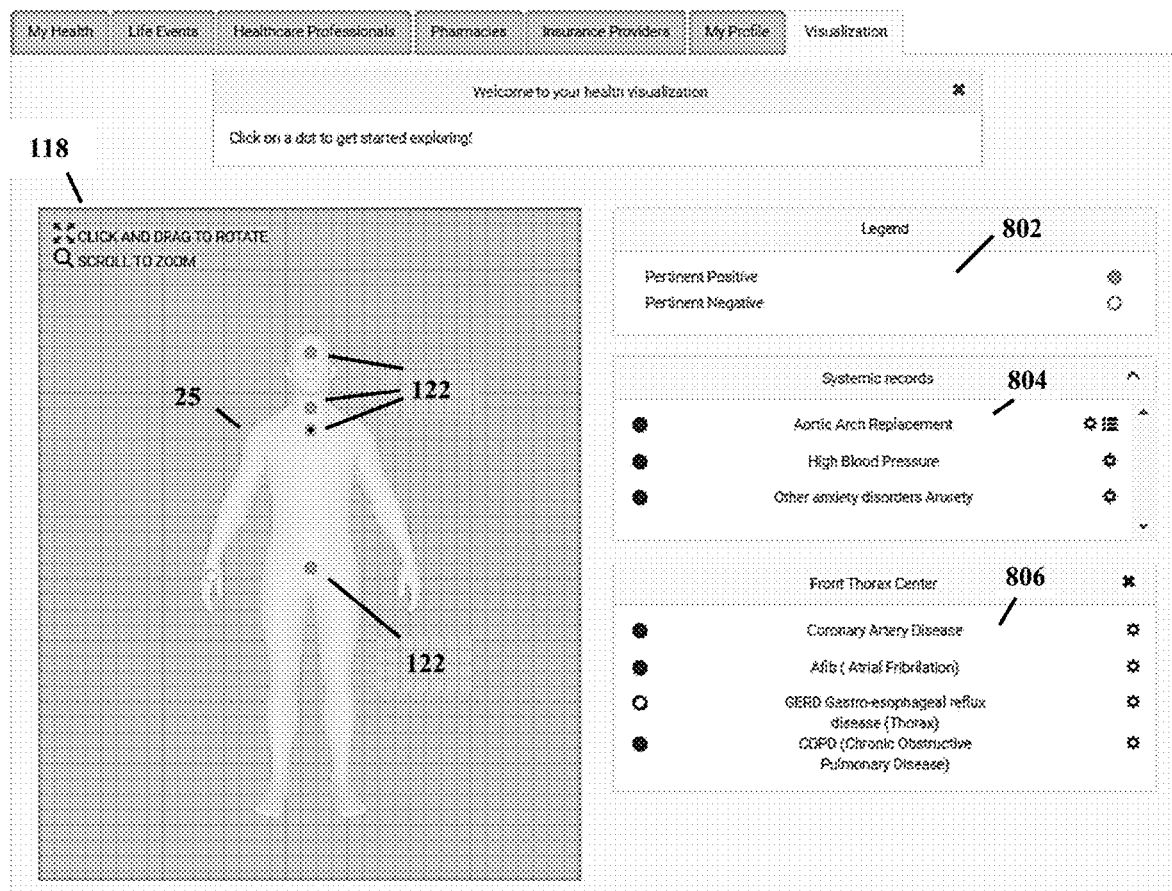

FIG. 8B is a screenshot depicting an exemplary visual mapping module 118 configured to provide a 3-D visual output of the patient's anatomy with the patient's health data and life event details. The depicted three-dimensional patient's anatomy includes the health history model 25, depicted at least in FIG. 1A, FIG. 6B, and FIG. 6C. The visual mapping module 118 displays indicators 122 on the 3-D visual output patient's anatomy. The user is able to view the specific mapped diagnosis by clicking on indicators 122 automated by the data on the anatomy. The depicted visual mapping module 118 display includes the pertinence indication 802 (positive or negative), systemic records 804 and user-selected records 806. The depicted example systemic records 804 include Aortic Arch Replacement, High Blood Pressure, and Anxiety. The depicted example user-selected records 806 include Coronary Artery Disease, Atrial Fibrillation, Gastro-esophageal reflux disease, and Chronic Obstructive Pulmonary Disease, associated with the Front Thorax Center body location selected in the user interface.

Figure 8C:
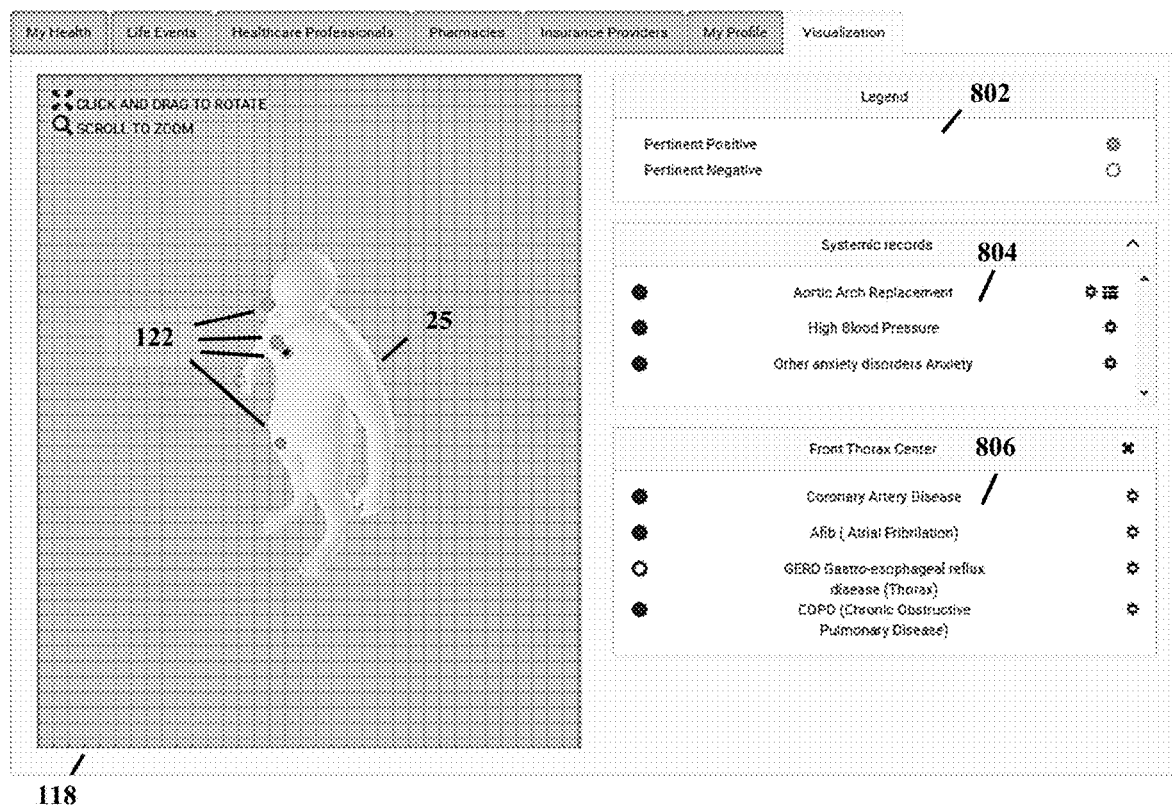

FIG. 8C is a screenshot depicting an exemplary visual mapping module 118 configured to provide a 3-D visual output of the patient's anatomy with the patient's health data and life event details. The depicted three-dimensional patient's anatomy includes the health history model 25, depicted at least in FIG. 1A, FIG. 6B, and FIG. 6C. In the depicted example, the 3-D visual output of the patient's anatomy has been reoriented different from the positions depicted by FIGS. 8A-8B. The 3-D visual output of the patient's anatomy has been reoriented in response to user input, to facilitate user visual access to various body locations. The visual mapping module 118 displays indicators 122 on the 3-D visual output patient's anatomy. The user is able to view the specific mapped diagnosis by clicking on indicators 122 automated by the data on the anatomy. The depicted visual mapping module 118 display includes the pertinence indication 802 (positive or negative), systemic records 804 and user-selected records 806. The depicted example systemic records 804 include Aortic Arch Replacement, High Blood Pressure, and Anxiety. The depicted example user-selected records 806 include Coronary Artery Disease, Atrial Fibrillation, Gastro-esophageal reflux disease, and Chronic Obstructive Pulmonary Disease, associated with the Front Thorax Center body location selected in the user interface.

Figure 8D:
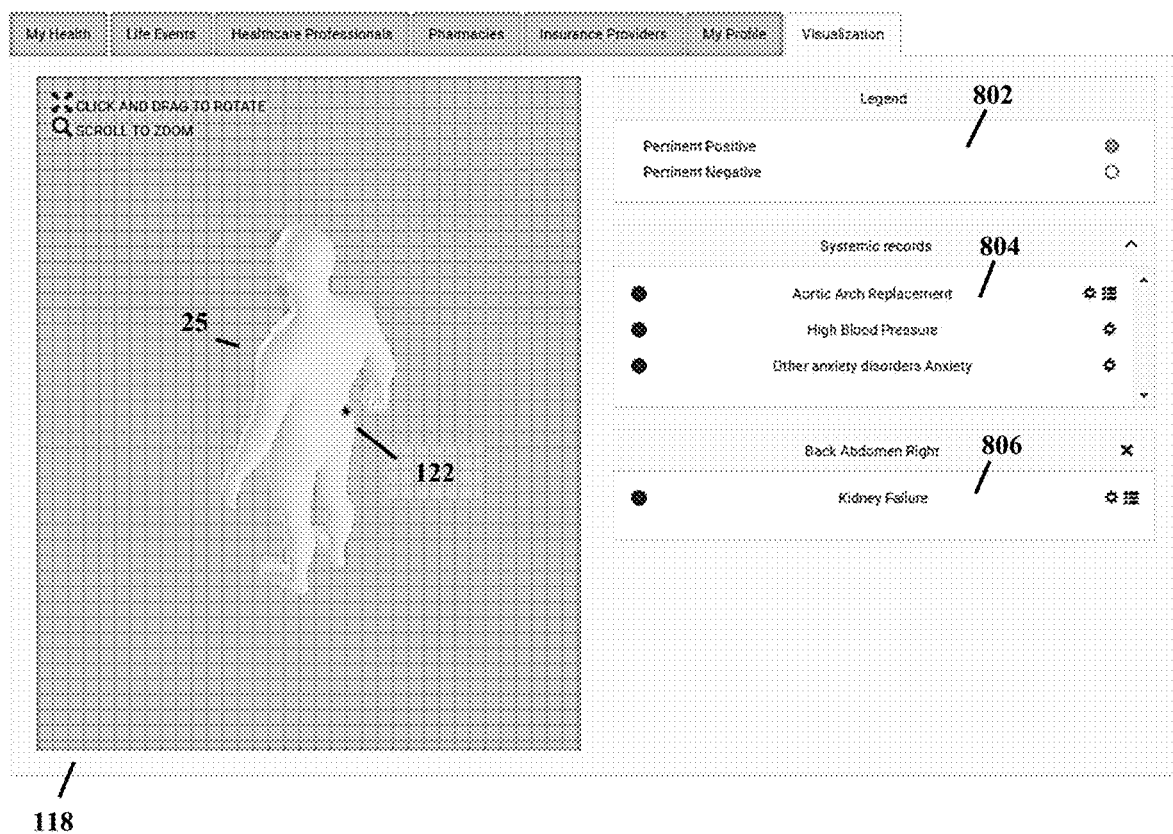

FIG. 8D is a screenshot depicting an exemplary visual mapping module 118 configured to provide a 3-D visual output of the patient's anatomy with the patient's health data and life event details. The depicted three-dimensional patient's anatomy includes the health history model 25, depicted at least in FIG. 1A, FIG. 6B, and FIG. 6C. In the depicted example, the 3-D visual output of the patient's anatomy has been reoriented different from the positions depicted by FIGS. 8A-8C. The 3-D visual output of the patient's anatomy has been reoriented in response to user input, to facilitate user visual access to various body locations. The visual mapping module 118 displays indicators 122 on the 3-D visual output patient's anatomy. The user is able to view the specific mapped diagnosis by clicking on indicators 122 automated by the data on the anatomy. The depicted visual mapping module 118 display includes the pertinence indication 802 (positive or negative), systemic records 804 and user-selected records 806. The depicted example systemic records 804 include Aortic Arch Replacement, High Blood Pressure, and Anxiety. The depicted example user-selected records 806 include Kidney Failure, associated with the Back Abdomen Right body location selected in the user interface.

Although various embodiments have been described with reference to the Figures, other embodiments are possible. For example, an embodiment system for managing and displaying health related data of a patient is provided, the system comprising: a database configured to store plurality of modules; and a processing unit coupled to the database to process the plurality of modules; a graphical user interface coupled to the processing unit to display the processed plurality of modules, wherein the plurality of modules comprises: a patient registration module configured to register the patient's personal information on the database; a life event module configured to receive patient's life event details related to health issues; a healthcare professional module configured to receive patient's healthcare professional information; a historical health data module configured to receive patient's historical health data; and a visual mapping module configured to provide a three-dimensional visual output of the patient's anatomy mapped with the patient's health data and life event details.

In accordance with teachings of the present disclosure, a system for managing and displaying health related data of a patient may include a database, a processing unit, and a graphical user interface. The database may be configured to store a plurality of modules. The processing unit may be coupled to the database to process the plurality of modules. A graphical user interface may display the processed plurality of modules.

In an embodiment according to the present disclosure, the plurality of modules includes a patient registration module, a life event module, a healthcare professional module, a historical health data module and a visual mapping module. The patient registration module may be configured to register the patient's personal information on the database.

The life event module may be configured to receive the patient's life event details related to health issues. The healthcare professional module may be configured to receive the patient's healthcare professional information. The historical health data module may be configured to receive the patient's historical health data. The visual mapping module may be configured to provide a three-dimensional visual output of the patient's anatomy mapped with the patient's health data and life event details.

Some embodiments may generally relate to managing and displaying health history of a user, and relate more particularly to managing and displaying health history on a virtual anatomy of a user.

In a January 2019 article in the New England Journal of Medicine, Schulman and Richman posit that innovation in electronic health records (EHRs) to meet Affordable Care Act (ACA) requirements has largely failed. (Schulman & Richman, 2019). Schulman and Richman suggest that policymakers and the health care industry are missing the mark by focusing on the organizational structure of physicians and hospitals and ignoring consumers' needs and innovative technologies. Schulman & Richman also note that one of the requirements of the ACA was for hospital systems and physicians to adopt EHRs that provide patients access to their own medical records.

At present, there are numerous options for health care providers to utilize electronic health records as billing systems, but very few options for the patient, parent, or guardian to maintain their own records in a thorough, quick, simple, and visually compelling manner. However, none among the medical history record services company are actively working, and none offered the unique organizational process and visual output to easily understand the medical history of patient.

Therefore, there is a need of a system for providing access to the patient/user direct access to their health history, not limited to medical care but dental, ophthalmic, mental, and specialist care, as well as prescription history, lab tests and results, insurance provider information, family history, childhood illnesses, immunization records, legal documents such as end-of-life directives, do not resuscitate directives, legal guardianship letters, and any other documents related to the care and well-being of a user. The invention is comprehensive, flexible, and allows users to add descriptive information as well as personal, financial, and legal documentation relating to all aspects of their health history in one unique system.

With new requirements of electronic health records systems, doctors and health care providers are frequently tasked with sifting through hundreds of pages of data regarding a patient. Kyle Murphy (Murphy) notes this obstacle to effective patient care in his article Improving Clinical Data Integrity Through EHR Documentation. Due to ACA requirements, much of this data is based on billing points or insurance record keeping needs. The records systems have little to do with patient health history and effective patient care. In many cases the information in a records system is limited to the care provided at a specific physician's office or health care facility, it may not include the records of specialists that are outside of a designated health care system. This reduces the amount of time that the clinician may be able to spend with the patient and can hinder the care to be provided.

Murphy also states that according to a 2015 Medicare/Medicaid Study "documenting a patient's records with all relevant and important facts, and having that information readily available, allows providers to furnish correct and appropriate services that can improve, quality, safety, and efficiency." With each new visit to a health care provider, the patient is routinely tasked with entering their health history in a different records system. Many systems do not interface with the systems of other health care providers or health facilities. This means the patient may spend more time trying to remember their health history or that of a loved one rather than getting quality time with a doctor or specialist. This can be a frustrating experience for many patients, caregivers, parents, or guardians. The patient/user spends more time navigating intake processes, providing financial and insurance information than with the actual medical professional.

Murphy also notes that the American Medical Informatics Association (AMIA) posits, "Clinician time is better spent diagnosing and treating patients," and that, "Regulatory guidance stipulating that data may be populated by others on the care team, including patients, would reduce this burden." Allowing the patients to add their own 'narratives' to their health records provides space for important aspects of the patient background that may assist in the care provided by the clinician.

Physician's themselves lament on the burdensome requirements of Electronic Health Records (EHRs). In December 2018, the journal Medical Economics surveyed their physician readers, asking them: "What's ruining medicine for physicians?" Their top-three answers: Paperwork and administrative burdens; Difficulty using EHRs; and, Government Regulations." (Medical Economics Staff, 2018) The article goes on to note that many EHRs are mandated with "auto-populated junk, no one wants to read," obscuring the critical information in patient records the clinician needs to read.

An adult-child may not know the health history of their elderly parent who presently needs their assistance for care and interaction with a health care provider. The care-giver may have to make critical care decisions or provide background to the clinician and would be unable to effectively do so, in some cases, hindering the care of the patient. With this invention, the health history is readily available by the user to share with their family member or health care provider.

A divorced parent or a custodial grandparent may not have complete information about a child's or grandchild's health history, accidents, provider visits, or immunization records. Parents and students may quickly provide to education institutions required immunization histories, prescriptions, and other specified health records instantly without costly and time-consuming records duplication requests from numerous health care providers. In the instances of an infectious disease outbreak, a student would be able to quickly provide accurate immunization records that can be stored on various embodiments of the disclosure.

Active Duty military personnel may use the invention to be aware of health issues of spouses or children that occurred during their deployment, giving them peace of mind. Retired military personnel who use VA and private health care services may easily share their health records between facilities where they receive care and where their records may not be readily available. This invention aligns with the MISSION Act, recently passed by Congress allowing Veteran's to seek and obtain health care services in their own communities outside of the VA system or inside the VA system as they see fit.

These are just a few examples of user profiles that could greatly benefit from this type of patient-centered data architecture, allowing for innovative and responsive approaches to care. Therefore, there is a need of a system for managing and displaying health history of a user. Some embodiments may provide a visual output system that a patient/user quickly share with their healthcare provider allowing the clinician more time for patient care.

In the Summary above and in this Detailed Description, and the Claims below, and in the accompanying drawings, reference is made to particular features of various embodiments of the invention. It is to be understood that the disclosure of embodiments of the invention in this specification is to be interpreted as including all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. Embodiments of the invention may be capable of myriad modifications in various obvious aspects, all without departing from the spirit and scope of the embodiment. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations," "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

In the present disclosure, the term "any" may be understood as designating any number of the respective elements, that is, as designating one, at least one, at least two, each or all of the respective elements. Similarly, the term "any" may be understood as designating any collection(s) of the respective elements, that is, as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

The Abstract is provided to comply with 37 C. F. R. § 1.72(b), to allow the reader to quickly ascertain the nature of the technical disclosure and is submitted with the understanding that it will not be used to interpret or limit the scope or meaning of the claims.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)—(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f). Elements recited in means-plus-function format are intended to be construed in accordance with 35 U.S.C. § 112 (f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed embodiment. Thus, the claims following this Detailed Description are hereby expressly incorporated into this Detailed Description, with each claim standing on its own as a separate embodiment. This disclosure is to be interpreted as including all permutations of the independent claims with their dependent claims.

According to an embodiment of the present invention, the system and method may be accomplished through the use of one or more computing devices. As depicted, for example, at least in FIG. 1A, FIG. 1B, FIG. 2, and FIG. 3, one of ordinary skill in the art would appreciate that an exemplary system appropriate for use with embodiments in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with embodiments of the present invention include, but are not limited to, proprietary computing devices, personal computers, mobile computing devices, tablet PCs, mini-PCs, servers or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and embodiments of the present invention are contemplated for use with any computing device.

In various embodiments, communications means, data store(s), processor(s), or memory may interact with other components on the computing device, in order to effect the provisioning and display of various functionalities associated with the system and method detailed herein. One of ordinary skill in the art would appreciate that there are numerous configurations that could be utilized with embodiments of the present invention, and embodiments of the present invention are contemplated for use with any appropriate configuration.

According to an embodiment of the present invention, the communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, BLUETOOTH connections, or any combination thereof. One of ordinary skill in the art would appreciate that there are numerous communications means that may be utilized with embodiments of the present invention, and embodiments of the present invention are contemplated for use with any communications means.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

Traditionally, a computer program consists of a sequence of computational instructions or program instructions. It will be appreciated that a programmable apparatus (i.e., computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable, and replaceable, or fixed. It will also be understood that a computer can include a Basic Input/output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the invention as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, and the like, or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, embodiments that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, embodiments of the invention are not described with reference to any particular programming language. It is appreciated that a variety of programming languages may be used to implement the present teachings as described herein, and any references to specific languages are provided for disclosure of enablement and best mode of embodiments of the invention. Embodiments of the invention are well suited to a wide variety of computer network systems over numerous topologies. Within this field, the configuration and management of large networks include storage devices and computers that are communicatively coupled to dissimilar computers and storage devices over a network, such as the Internet.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A process, comprising:
    receiving, by an application server, a patient health record from a doctor's mobile device;
    determining, by the application server, a medical condition relationship between the health record and patient health history, wherein the health history comprises a plurality of linked health records, and wherein the relationship is determined based on comparing data encoded by the received health record with data encoded by the linked health records forming the health history;
    updating, by the application server, the health history to link the received health record with the patient health history in an order based on the medical condition relationship and a condition degree of severity determined as a function of the received health record, to visually present conditions in order of severity as the linked health history is automatically traversed in response to user input;
    determining, by the application server, a condition associated with the received health record;
    receiving, from a user interface of the doctor's mobile device a designation of the pertinence of the condition to the received health record, wherein the user interface is configured with a pertinence selector, and wherein the pertinence of the condition to the received health record is designated pertinence positive or pertinence negative based on user operation of the pertinence selector;
    determining, by the application server, a location on the patient's body affected by the condition; and,
    automatically traversing, by the application server, the updated health history in response to user input, and visually presenting in the user interface of the doctor's mobile device the medical condition relationship between the health record and health history based on the condition, wherein the visually presented relationship includes the designation received from the user interface of the doctor's mobile device of the pertinence of the condition to the health record.

2. The process of claim 1, wherein presenting the relationship between the health record and health history based on the condition further comprises the patient's health history interactively visualized on a model of the patient's body.

3. The process of claim 2, wherein the patient's health history interactively visualized on the model of the patient's body further comprises the model of the patient's body visibly marked to indicate the location on the patient's body affected by the condition associated with the health record.

4. The process of claim 3, wherein the model of the patient's body visibly marked to indicate the location on the patient's body affected by the condition associated with the health record further comprises the marked location on the visualized model clickable to display when clicked a health record medically related to the patient condition.

5. The process of claim 1, wherein determining the condition associated with the health record further comprises categorizing the condition as systemic or non-systemic, and presenting the relationship between the health record and health history further comprises presenting a systemic condition marked visually distinct from a non-systemic condition on a model of the patient's body.

6. The process of claim 5, wherein updating the health history further comprises linking systemic conditions in order before non-systemic conditions, to visually present systemic conditions before non-systemic conditions as the linked health history is automatically traversed in response to user input.

7. The process of claim 1, wherein the process further comprises denying health history access to the user interface of the doctor's mobile device until successful authentication of the doctor by the user, wherein the authentication is determined as a function of a QR code visually transmitted by the user during a telemedicine session.

8. The process of claim 1, wherein determining the condition associated with the health record further comprises determining a condition degree of severity, and presenting the relationship between the health record and health history further comprises visibly marking a model of the patient's body to present a more severe condition as visually distinct from a less severe condition, based on the degree of severity.

9. The process of claim 1, wherein presenting the relationship between the health record and health history based on the condition further comprises evaluating the condition to determine if the condition medically complicates another condition in the health history.

10. An apparatus, comprising:
a processor;
a user interface, operably coupled with the processor; and,
a memory, operably coupled with the processor, wherein the memory encodes processor executable program instructions and data to program and configure the processor to cause the apparatus to perform operations comprising:
receive a patient health record comprising a plurality of data fields encoding patient health information;
determine a medical condition relationship between the received health record and patient health history, wherein the health history comprises a plurality of linked health records, and wherein each health record of the plurality of linked health records comprising the health history comprises a plurality of data fields encoding patient health information, and wherein the relationship between the received health record and the patient health history is determined as a function of comparing the received health record with at least a portion of the plurality of linked health records comprising the health history;
determine a medical condition and a condition degree of severity associated, with the received health record and a location on the patient's body affected by the condition;
receive, from the user interface a designation of the pertinence of the condition to the received health record, wherein the user interface is configured with a pertinence selector, and wherein the pertinence of the condition to the received health record is designated as pertinence positive or pertinence negative based on user operation of the pertinence selector;
categorize the medical condition as systemic or non-systemic based on medical diagnosis data encoded by the received health record, wherein the categorization is determined as a function of comparing the diagnosis data encoded by the received health record with predetermined data representative of possible diagnoses;
update the health history by linking the received health record with the health history in an order based on the medical condition relationship between the received health record and the linked health records comprising the health history, based on associating patient health information encoded by the received health record with patient health information encoded by at least one health record comprising the health history, wherein systemic conditions are linked in order of condition severity, to visually present systemic conditions in order of severity as the linked health history is automatically traversed in response to user input; and,
automatically traversing the updated health history in response to medical condition name input by a user to present in the user interface the medical condition relationship between the received health record and health history interactively visualized on a model of the patient's body, wherein the relationship is based on the condition, and wherein the relationship presented in the user interface includes display of the pertinence positive or pertinence negative designation received from the user interface and the location on the patient's body affected by the condition, visibly marking the model of the patient's body to indicate the location on the patient's body affected by the condition associated with the health record.

11. The apparatus of claim 10, wherein the plurality of linked health records comprising the health history are linked to form a collection of health records associated based on comparing data encoded by the patient health information data fields between the health records.

12. The apparatus of claim 11, wherein the data compared between the health records further comprises diagnosis data.

13. The apparatus of claim 11, wherein the data compared between the health records further comprises procedure data.

14. The apparatus of claim 11, wherein the data compared between the health records further comprises life event data.

15. The apparatus of claim 10, wherein the operations performed by the apparatus further comprise: in response to detecting in the user interface a selection of an affected patient body location marked on the model of the patient's body, displaying in the user interface a user selectable list of the linked health records comprising the health history associated with the selected location.

16. The apparatus of claim 10, wherein the operations performed by the apparatus further comprise: in response to detecting in the user interface a user engagement with a user interface control governing orientation of the model of the patient's body, display the model of the patient's body reoriented as a function of the user engagement with the orientation control.

17. An apparatus, comprising:
a processor;
a user interface, operably coupled with the processor; and,
a memory, operably coupled with the processor, wherein the memory encodes processor executable program instructions and data to program and configure the processor to cause the apparatus to perform operations comprising:

receive a patient health record comprising a plurality of data fields encoding patient health information, wherein the patient health record encodes data indicating a pertinence of a condition to the received health record, and wherein the encoded pertinence of the condition to the received health record is pertinence positive or pertinence negative;

determine a medical condition relationship between the received health record and health history, wherein the health history comprises a plurality of linked health records, wherein each health record of the plurality of linked health records comprising the health history comprises a plurality of data fields encoding patient health information, wherein the relationship between the received health record and the patient health history is determined as a function of comparing the received health record with at least a portion of the plurality of linked health records comprising the health history, wherein the plurality of linked health records comprising the health history are linked to form a collection of health records associated based on comparing data encoded by the patient health information data fields between the health records, and wherein the data compared between the health records further comprises at least one of: diagnosis, pertinence, procedure, life event, condition, complicating condition, or onset date data;

determine a medical condition and a condition degree of severity associated with the received health record and a location on the patient's body affected by the condition;

categorize the medical condition as systemic or non-systemic based on medical diagnosis data encoded by the received health record, wherein the categorization is determined as a function of comparing the diagnosis data encoded by the received health record with predetermined data representative of possible diagnoses;

update the health history by linking the received health record with the health history in an order based on the medical condition relationship between the received health record and the linked health records comprising the health history, based on associating patient health information encoded by the received health record with patient health information encoded by at least one health record comprising the health history, wherein systemic conditions are linked in order of condition severity, to visually present systemic conditions in order of severity as the linked health history is automatically traversed in response to user input;

automatically traversing the updated health history to present in the user interface the medical condition relationship between the received health record and health history interactively visualized on a model of the patient's body, wherein the relationship is based on the condition and a location on the patient's body affected by the condition, visibly marking the model of the patient's body to indicate the location on the patient's body affected by the condition associated with the health record and the indication encoded by the health record of the pertinence of the condition to the health record as the health history is traversed in response to medical condition name user input, and wherein in response to determining the relationship between the received health record and health history includes life event data designated as pertinent positive to the condition associated with the health record, visibly marking the model to display the pertinent positive life event data;

in response to detecting in the user interface a selection of an affected patient body location marked on the model of the patient's body: displaying in the user interface a user selectable list of the linked health records comprising the health history associated with the selected location; and, in response to detecting in the user interface a user engagement with a user interface control governing orientation of the model of the patient's body, display the model of the patient's body reoriented as a function of the user engagement with the orientation control.

18. The apparatus of claim 17, wherein at least a portion of the operations performed by the apparatus are implemented by a SaaS (Software as a Service) application executing as a cloud service.

19. The apparatus of claim 17, wherein the operations performed by the apparatus further comprise denying health history access to a user until successful authentication by the user.

20. The apparatus of claim 19, wherein authentication is determined as a function of a QR code visually transmitted as a function of telemedicine.

* * * * *